United States Patent
Pierson et al.

(10) Patent No.: US 9,668,835 B2
(45) Date of Patent: Jun. 6, 2017

(54) TISSUE MANAGEMENT IMPRESSION MATERIAL AND DISPENSING SYSTEMS

(71) Applicant: DENTSPLY INTERNATIONAL INC., York, PA (US)

(72) Inventors: Paul Richard Pierson, Camden, DE (US); Fuming Sun, Middletown, DE (US); Richard James Bennett, Milford, DE (US); Robert J. Pieroni, Milford, DE (US)

(*) Notice: Subject to any disclaimer, the term of this patent is extended or adjusted under 35 U.S.C. 154(b) by 0 days.

(21) Appl. No.: 14/818,005

(22) Filed: Aug. 4, 2015

(65) Prior Publication Data

US 2015/0335405 A1  Nov. 26, 2015

Related U.S. Application Data

(62) Division of application No. 13/530,516, filed on Jun. 22, 2012, now Pat. No. 9,283,059.

(60) Provisional application No. 61/499,875, filed on Jun. 22, 2011.

(51) Int. Cl.
*A61C 9/00* (2006.01)
*A61C 13/15* (2006.01)

(52) U.S. Cl.
CPC .......... *A61C 9/0026* (2013.01); *A61C 9/0006* (2013.01); *A61C 19/004* (2013.01)

(58) Field of Classification Search
CPC .......... A61C 9/0026; A61C 5/04; A61C 5/06; A61C 5/062; A61C 5/064; A61C 5/066; A61C 5/068; B65D 81/3205; B65D 81/3211; B65D 81/3216; B65D 81/3222; B65D 81/3227; B65D 81/3233; B65D 81/3238; B65D 81/3244; B65D 81/325; B65D 81/3255; B65D 81/3261; B65D 81/3266; B65D 81/3272; B65D 81/3277; B65D 81/3283; B65D 81/3288; B65D 81/3294
USPC ....... 433/80, 82, 88–90, 126, 125, 214, 213; 604/82, 140–141, 143–147; 222/386.5, 222/389, 334, 145.5, 145.6, 129, 135–136
See application file for complete search history.

(56) References Cited

U.S. PATENT DOCUMENTS

| | | | | |
|---|---|---|---|---|
| 3,521,356 A | * | 7/1970 | Newman | A61O 5/062 433/89 |
| 3,548,500 A | * | 12/1970 | Cohen | A61C 9/00 433/218 |
| 4,255,140 A | * | 3/1981 | Marshall | A61C 9/00 222/575 |
| 4,468,202 A | | 8/1984 | Cohen | |
| 4,531,914 A | | 7/1985 | Spinello | |
| 5,190,457 A | * | 3/1993 | Schreinemakers | A61C 9/0006 433/214 |

(Continued)

FOREIGN PATENT DOCUMENTS

EP  2230025 A1  9/2010
GB  2142245 A  1/1985

(Continued)

*Primary Examiner* — Yogesh Patel
(74) *Attorney, Agent, or Firm* — McNees Wallace & Nurick LLC

(57) ABSTRACT

Disclosed herein are a tissue management impression material and a method of application into the sulcus of a patient, whereby the tissue management impression material is a part of the final dental impression made when manufacturing a dental device, such as a crown.

14 Claims, 23 Drawing Sheets

(56) References Cited

U.S. PATENT DOCUMENTS

| | | | |
|---|---|---|---|
| 5,661,222 A | 8/1997 | Hare | |
| 5,807,100 A * | 9/1998 | Thornton | A61C 9/00 128/862 |
| 5,848,894 A * | 12/1998 | Rogers | A61O 5/064 433/90 |
| 5,863,965 A | 1/1999 | Hare | |
| 6,116,905 A * | 9/2000 | Hoos | A61C 9/00 264/16 |
| 6,170,714 B1 | 1/2001 | Lesage | |
| 6,182,867 B1 | 2/2001 | Keller | |
| 6,422,865 B1 * | 7/2002 | Fischer | A61O 5/02 433/81 |
| 6,988,892 B2 * | 1/2006 | Dragan | A61O 5/062 433/90 |
| 7,195,483 B2 * | 3/2007 | Dragan | A61C 9/0033 433/136 |
| 7,549,862 B2 * | 6/2009 | Kollefrath | A61C 9/0033 433/136 |
| 2001/0004082 A1 | 6/2001 | Keller et al. | |
| 2007/0184410 A1 | 8/2007 | Boghosian | |
| 2007/0264315 A1 | 11/2007 | Fournie et al. | |
| 2008/0041879 A1 * | 2/2008 | Pierson | A61O 5/062 222/137 |
| 2008/0041887 A1 | 2/2008 | Scheindel | |
| 2008/0220050 A1 | 9/2008 | Chen et al. | |
| 2010/0248188 A1 * | 9/2010 | Sefidroodi | A61C 9/00 433/201.1 |
| 2010/0248190 A1 | 9/2010 | Chen et al. | |
| 2010/0285485 A1 | 11/2010 | Jung et al. | |
| 2011/0151403 A1 | 6/2011 | Pauser et al. | |
| 2011/0223556 A1 | 9/2011 | Abel | |
| 2013/0273495 A1 * | 10/2013 | Dragan | A61C 9/0033 433/81 |

FOREIGN PATENT DOCUMENTS

| | | |
|---|---|---|
| WO | 9009151 A1 | 8/1990 |
| WO | 9632088 A1 | 10/1996 |
| WO | 2007104037 A2 | 9/2007 |
| WO | 2007131371 A1 | 11/2007 |
| WO | 2009036962 A2 | 3/2009 |
| WO | 2009036963 A2 | 3/2009 |
| WO | 2010117442 A1 | 10/2010 |

\* cited by examiner

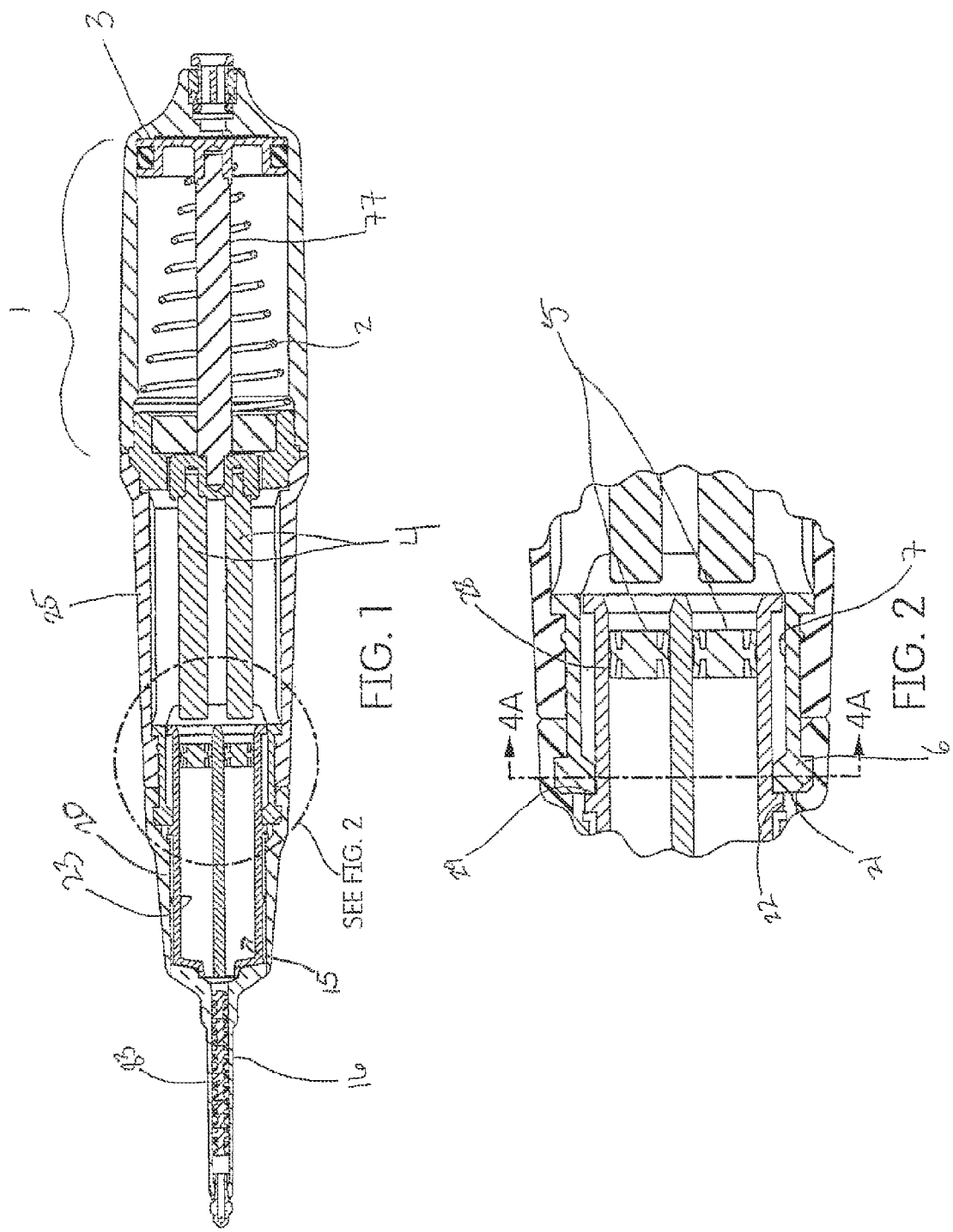

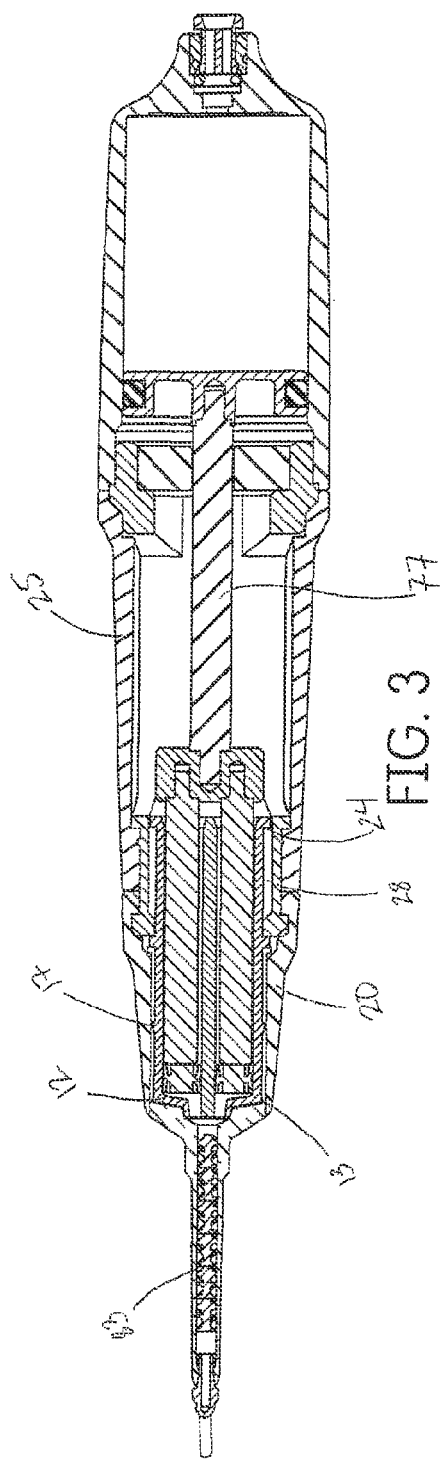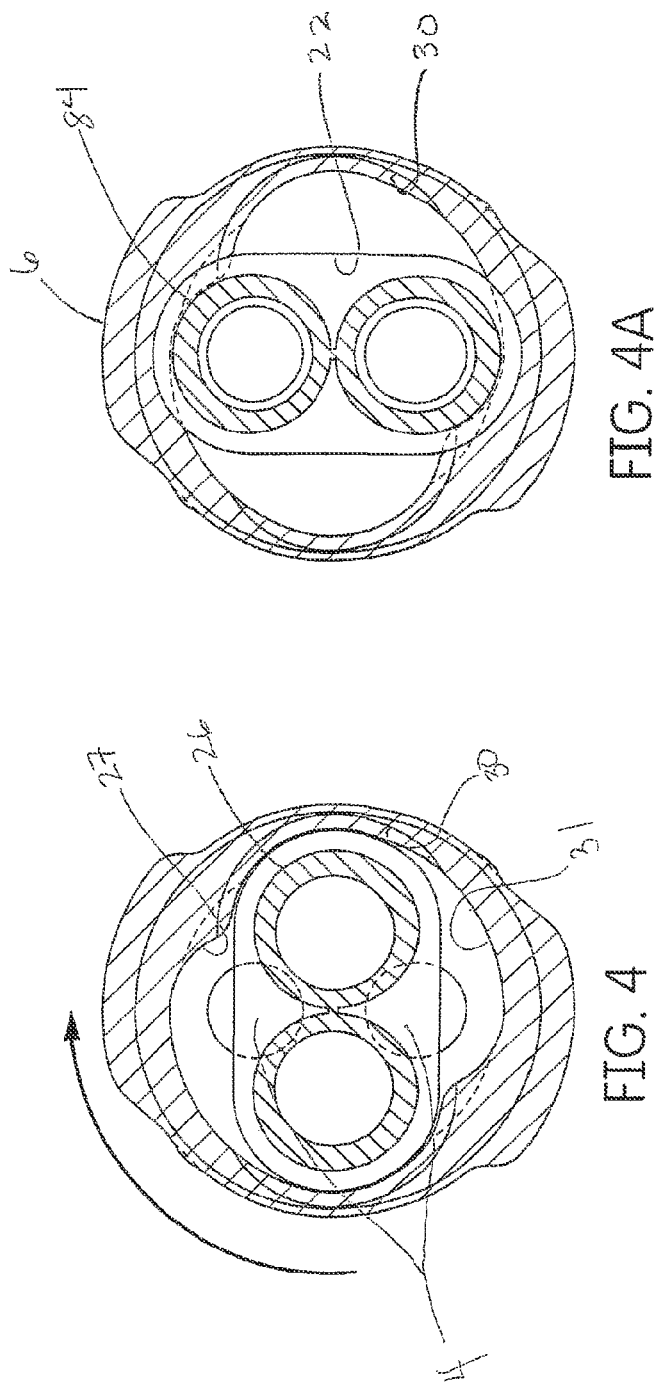

TISSUE MANAGEMENT IMPRESSION MATERIAL AND DISPENSING SYSTEMS

This application is a divisional of, and claims priority to, U.S. application Ser. No. 13/530,516 filed Jun. 22, 2012, which itself claims priority to U.S. Provisional Application No. 61/499,875, filed Jun. 22, 2011, both of which are hereby incorporated by reference in their entirety.

FIELD OF THE DISCLOSURE

Disclosed herein is a system useful for producing a cordless, dental impression necessary for the production of a dental device, such as a crown.

BACKGROUND

U.S. Publication No. 2011/0151403 describes for use in retracting a gingiva from a human tooth by widening a gingival sulcus with a clay-based dental composition. The device comprises a canula with a free end having an opening for dispensing the clay-based dental composition. The free end is shaped to be inserted with its front in the entry of the gingival sulcus, and to laterally displace the gingiva from the tooth as the canula is moved in the gingival sulcus.

U.S. Pat. Nos. 5,661,222 and 5,863,965, and EP 820 265 B1, describe vinylsiloxane impression material compositions which have improved tear strength and wettability, particularly for use in making dental impressions.

U.S. Pat. No. 4,468,202 describes a method for obtaining a dental impression of subgingival anatomy.

U.S. Pat. No. 7,195,483 relates to a method and a device for effecting the cordless retraction of the gingival sulcus tissue prior to taking an impression of a tooth for making a crown or bridge, which is attained by controlling any bleeding in the gingival sulcus area, and utilizing a dental dam preferably formed out of a sponge or foam like material to contain an astringent fortified silicone impression material embedded about the prepared tooth, and using the patient's biting force to apply the necessary pressure onto the dam until the silicone impression material sets and adheres to the dam to enhance easy removal of the set impression material from the tooth.

WO 2010/117442 describes a method and material for retracting gingival tissue using a material that contains an astringent and fluid absorbing agent.

U.S. Publication No. 2007/0184410, describes a method of taking a dental impression of dentition that includes preparing the dentition with a gingival retraction cord.

U.S. Pat. No. 6,170,714 describes a device that is intended for extruding a material from a reservoir through tubular applicator tip.

U.S. Pat. No. 4,255,140 describes a method and syringe that is used for taking an impression of a prepared tooth. A tube fits over the entire prepared tooth and premixed impression material is forced over the tooth and into the sulcus using the syringe. An impression tray is filled with material and placed over prep to pick up the syringed material, which becomes part of the final impression.

This method can cause voids if the user prematurely withdraws the tip.

U.S. Pat. No. 6,182,867 discloses a manually operated device that is useful for dispensing dental impression materials from dual chambered cartridges. The device is a mechanical handpiece with plungers that advance via a ratcheting mechanism. It is large and otherwise unsuited to precise delivery of small increments of material such as in this case.

WO 90/09151 describes two devices, one for packing retraction cord with a reciprocating placement tool (hammer), and the second embodiment is a syringe-like instrument that extrudes premixed impression material from a single syringe barrel through a rotatable applicator tip.

U.S. Pat. No. 4,531,914 describes a method for displacing the gingiva using a body of coherent flowable and moldable material to produce a dry gingival trough for impression taking. The moldable body can be formed of plastic thixotropic medium such as silicone putty, hydrocolloids and certain unpolymerized synthetic rubbers, certain gels and sol-gels, which can be rendered hydrosorbent by incorporating non-woven absorbent fibers such as wood fibers, cotton fibers or the like.

WO 2007/104037 describes a capsule (cartridge) with a preassembled mixtip that pivots from a closed position to an open position. The pivot axis is described as being transverse to the longitudinal axis of the capsule body.

WO 2009/036963 describes a unit-dose delivery cartridge for storing and discharging two components using a discharge gun. The mixer is pre-installed on the cartridge and the cartridge can be opened without uninstalling the mixer.

U.S. Publication No. 2007/0264315A1 relates to a biocompatible paste containing an aqueous excipient, useful as bandage for mucous membranes of the oral cavity or on the skin, including natural kaolin, a humectant, e.g., propylene glycol, and a hydrogel forming agent, e.g., cellulose.

U.S. Publication No. 2008/0220050A1 relates to a gingival retraction paste composition useful for widening and treating gingival sulcus. The composition comprises clay, micronized glass filler, astringent agent and water.

U.S. Publication No. 2010/0248190A1 describes a method for temporarily widening gingival sulcus, by inserting uncured composition within gingival sulcus for widening, maintaining the composition in the gingival sulcus, and photo curing the uncured composition in order to provide a cured composition.

U.S. Publication No. 2011/0223556 describes a sulcus impression tip for use in injecting dental impression material for making dental impressions. The apparatus includes a body having a gripping portion and a discharge tip. The body includes a needle canula in fluid communication with a flange, wherein the flange receives and holds the dental impression material and is secured in the interior surface of the gripping portion. The discharge tip has a bore there through which permits a friction fit with the outside diameter of needle canula. The length of the needle canula is approximately longer than the length of the discharge tip. The body further defines an angle such that when the dentist is holding the gripping portion, the angle permits the discharge tip and needle canula to be positioned for easy access in the oral cavity by the dentist. The discharge tip is sized and shaped to effectively separate the gum from the tooth in the selected region so that the needle canula is positioned to permit exact positioning for placement of the dental impression material along the sulcus.

U.S. Publication No. 2010/0285485 describes an air driven impression syringe designed to be held with a pen type grip and capable of precise placement of impression material. An embodiment of the device is a dental tool useful in the fabrication of dental prostheses capable of extruding impression material comprising a cylindrical grip body with two ends, an air-driven piston with a center rod; and where the cylindrical body defines a bore to accept the air driven piston, a channel on one end of the syringe and a source of pressurized air. The syringe includes a disposable tip preloaded with dental impression material attached to the channel such that a second bore in said syringe tip containing dental impression material aligns with the rod and wherein the rod can extend beyond the end of the body into the second bore to extrude material from the tip.

SUMMARY

The system disclosed herein comprises an air powered pneumatic dispenser that aids in precision placement of a tissue management impression material that accurately records the dental anatomy in a negative impression technique.

The system disclosed herein is of particular use with dental materials where precision placement is critical to a successful medical procedure. As such, the device may have utility with the delivery of restorative dental products such as dual-cure or self-cure resins for impression taking, bleaching materials, various crown and bridge materials, cements, endodontic materials for treating root canals, dental restoratives, application of anesthetics, periodontal materials and dental lab products. In addition, the device itself may have utility with pharmaceutical or medical products that also require precision placement coupled with powered delivery.

Disclosed herein is an application device and tissue management impression material that may be applied into the sulcus of a patient when preparing an impression of a prepared tooth for the manufacture of a dental device, such as a crown. In combination, the device and tissue management impression material comprise a method for precisely depositing said material into the sulcus to accurately record the anatomy in a cordless impression technique.

Typically, dentists use retraction cord or clay based retraction pastes to laterally displace the gingiva. This is referred to as tissue retraction and it provides a space for impression materials when taking a dental impression. Retracting the gingiva with cord is painful for the patient and traumatic to the tissue because the dentist must push it in with the edge of an instrument. Packing the cord retracts the sulcus and temporarily stops any hemorrhaging caused during tooth reduction. However, the cord is removed just before the impression and that usually causes hemorrhaging, which is counterproductive to achieving a satisfactory impression. A current alternative to packaging cord is clay based retraction pastes. Refraction pastes are generally regarded as effective in controlling the hemorrhaging but ineffective in tissue retraction because once the paste is rinsed away (prior to the impression), the tissue rebounds leaving little space between the tissue and the tooth, and resulting in an inadequate impression.

In embodiments, described herein are dental devices suitable for applying the tissue management impression material into the sulcus of a prepared tooth of a patient.

In yet further embodiments, described herein are methods of applying the tissue management impression material into the sulcus of a patient, whereby the tissue management impression material is a part of the final dental impression made when manufacturing a dental device, such as a crown.

The objective of the disclosed device, material, system and method is to dispense a tissue management impression material into the sulcus using a dispenser. The tissue management impression material will become part of the final impression and eliminates the need to use packing cord or clay based retraction pastes.

Another embodiment of the method is to let the tissue management impression material cure in place prior to seating a tray of impression material, which may referred to as a pickup technique. In yet another alternative embodiment, a self-curing tissue retraction material would be deposited into the sulcus and would be allowed to cure. The self-curing tissue retraction material would then be removed and would provide temporary retraction for a normal cordless impression technique.

BRIEF DESCRIPTION OF THE DRAWINGS

FIG. 1 is an assembly view of a pneumatic dispenser suitable for dispensing the tissue management impression material disclosed herein.

FIG. 2 shows a detailed view of FIG. 1.

FIG. 3 shows the dispenser shown in FIG. 1, with the plunger rods in an advanced position (the return spring has been omitted for clarity).

FIG. 4 is a cross section, which demonstrates the loading position of the cartridge shown in FIG. 1 and the initial relationship to the bayonet body and plunger rods of FIG. 4A.

FIG. 4A is a cross section of FIG. 2 and demonstrates the final position of the cartridge shown in FIG. 4 after 90° of rotation. Some components have been omitted from the cross section for clarity.

DESCRIPTION

Figure 5:
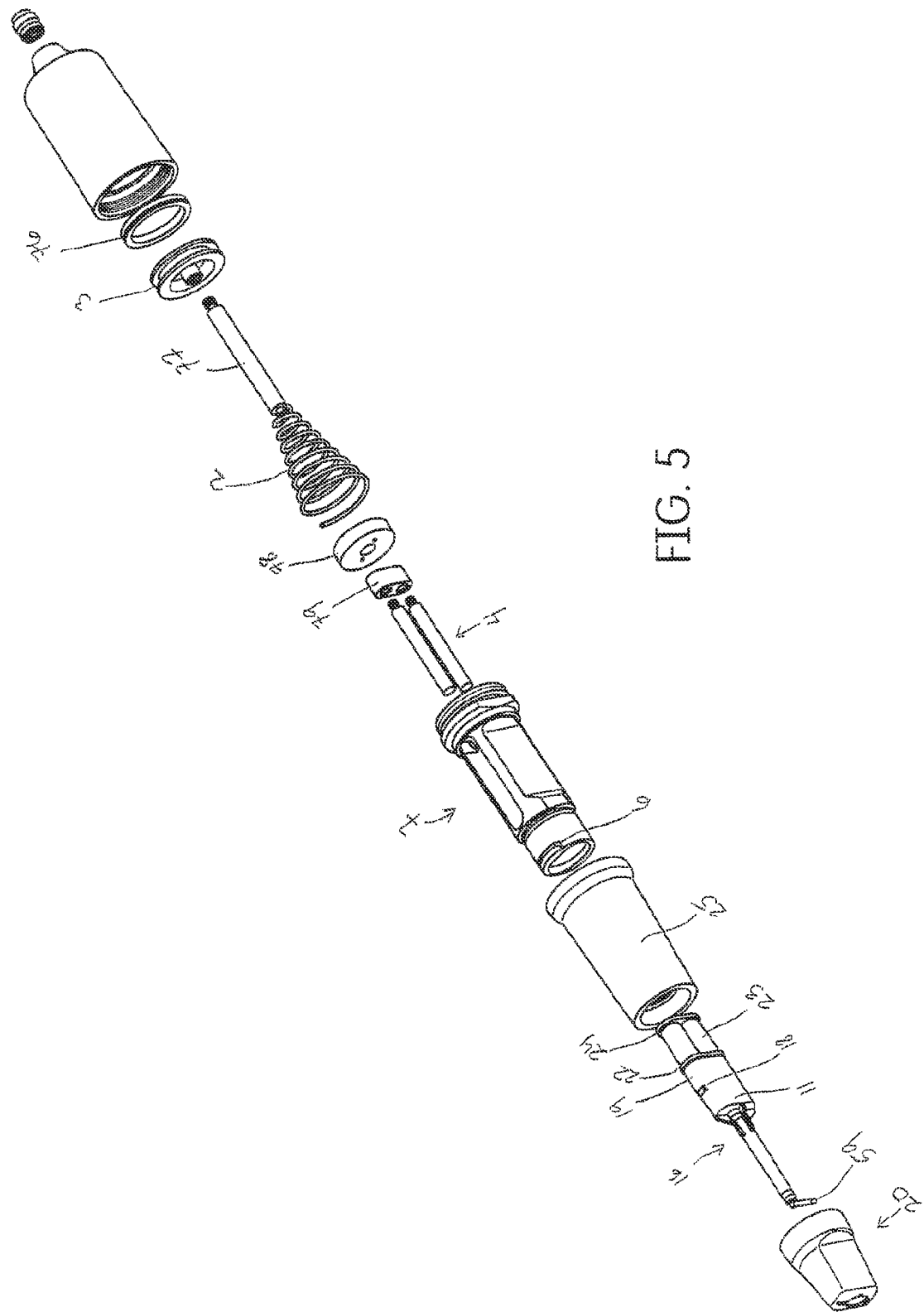
FIG. 5 shows an exploded assembly view of the dispenser of FIG. 1.

Disclosed herein is a system that comprises an air powered pneumatic dispenser that aids in precision placement of a dental material that may be accurately placed by a dental practitioner. In embodiments the dispenser may be used to place a tissue management impression material such that the material accurately records the dental anatomy in a negative impression technique.

The system disclosed herein is of particular use with dental materials where precision placement is critical to a successful medical procedure. As such, the device may have utility with the delivery of restorative dental products such as dual-cure or self-cure resins for impression taking, bleaching materials, various crown and bridge materials, cements, endodontic materials for treating root canals, dental restoratives, application of anesthetics, periodontal materials and dental lab products. In addition, the device itself may have utility with pharmaceutical or medical products that also require precision placement coupled with powered delivery.

Disclosed herein is a tissue management impression material that may be an elastomeric impression material, such as vinylsiloxane, polyether, polyacrylates, polysulfides, alginate, etc. For example, the viscosities of these materials may be described as monophase, heavy body or putty. In embodiments, the viscosity of the tissue management impression material may be any type elastomeric impression material, such as Type 0, 1, 2 or 3 as per ISO 4823 specification, it is preferred to use Type 1 or Type 2 elastomeric impression materials (as defined in ISO 4823) as tissue management impression material. The tissue management impression material suitable for use herein may be manufactured by any method of manufacturing any impression material, such as vinylsiloxane, polyether, polyacrylates, polysulfides, alginate, etc., impression materials. The procedure requires the tissue management impression material be compatible with associated elastomeric wash and tray impression materials.

The two component, room temperature vulcanization vinylpolysiloxane (VPS) materials which are capable of undergoing addition reactions are the most popularly used dental impression materials. The dental impression material may be a mixture of a diorganopolysiloxane containing terminal triorganosiloxy groups in which at least one vinyl group is present in each of the triorganosiloxy groups, an organopolysiloxane having at least three Si-bonded hydrogen atoms per molecule, an organoplatinum complex catalyst capable of promoting the addition of Si-bonded hydrogen to vinyl groups at room temperature and, if desired, additives such as fillers, pigments, flavoring substances and plasticizers. The diorganopolysiloxane of this type are those of the general formula:

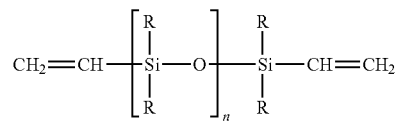

in which each R denotes an un-substituted or substituted monovalent hydrocarbon radical free of aliphatic multiple bonds, and n denotes an integer. The value of n should be such that the polymer has a viscosity of from 200 to 300,000 cPs at 25° C. The VPS impression materials in general have good dimensional accuracy and details, and resistance to deformation.

But in employing vinylpolysiloxane as dental impression materials, a number of difficulties have arisen, especially tear strength and wetting ability tend to be low. To remedy the problem, QM resins carrying vinyl groups are used. The letters Q and M stand for quadrafunctional and monofunctional monomers, which constitute the resins. The quadrafunctional hydrophilic chemistry combines a cross-linked polymer web with a proprietary surface active ingredient. The polymer web provides exceptional tear strength, and the proprietary surfactant has a wetting ability equivalent to polyether. This unique modified vinyl siloxane chemistry provides surface detail in a moist environment unmatched by traditional impression materials. It can capture deep sulcular margins and interproximal detail without tearing.

Polyether based two component formulations are another type of widely used impression material. The polyether is a linear chain built up by tetrahydrofuran/ethyleneoxide, the chain itself has hydrophilic properties which can be adjusted by the tetrahydrofuran/ethyleneoxide ratio, the aziridine moieties at the end of a linear polyether chain, which are also known as ethyleneimine compounds or substituted aziridines and aziridine derivatives, can be converted into highly molecular polyimine compounds by cross linking with an aromatic alkyl sulphonate by means of catalysts which introduce and thus initiate polymerization. Polymerization can be initiated by mixing the polymerization initiator with the aziridine compound at ambient temperature although temperatures above or below ambient may be utilized. The polyether impression materials in general have good wettability during work time, good dimensional accuracy and details, but have high permanent deformation, low tear strength, unpleasant taste and odor, and are hard to remove.

The urethane polyacrylate having at least one isocyanate acrylic pendent group provides an excellent dental composition component that is non-toxic when used in the oral cavity and will assume a permanent elastomeric memory when cured and to be used as an impression material. The impression material includes a free radical polymerizable resin, alkyl benzensulfonyl titanate, polymerization initiator and filler. The composition of matter in the form of a compound having the following general formula:

wherein R1 is

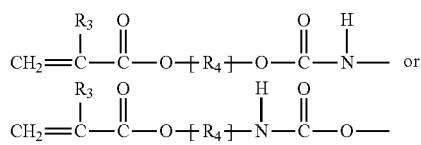

and R1 may be the same or different and each independently preferably have from 5 to 100 C, more preferably 5 to 15 C and most preferably 6 to 11 C. R3 is H, alkyl, sub alkyl, aryl, sub aryl, F, CN. R3 may be the same or different in each position. R4 is a divalent hydrocarbon radical or divalent sub hydrocarbon radical and may be straight or branched chain or cyclic or a combination thereof. [A] is any polyurethane, polyester or polyether oligomer. For example, [A] may be chosen to be a low molecular weight polyether when a relatively rigid polymer is desired, and [A] and other substituent may be chosen to have a high molecular weight when a relatively soft pliable polymer is desired. A preferred composition is where [A] is represented by [R5]-X—[R6]. X is a polyurethane and R5-X and R6-X are joined by a urethane or polyurethane linkage. X may broadly contains any hydrocarbon or sub hydrocarbon radical and may be straight or branched chain or cyclic or a combination thereof and may also be one or more of the following radicals: siloxane, sub siloxane, sulfone, etc., but is preferably a polyether or a polyester or a mixture thereof, most preferably X is a polyether and the polyether radical is a straight chain. R5 and R6 are each independently divalent hydrocarbon radicals or divalent sub hydrocarbon radicals and may be straight or branched chain or cyclic or a combination thereof and may also be siloxane or sub siloxane radicals. Sub or substituent is not limited to but is meant to include, as representative examples, radicals selected from the group consisting of halogen, lower alkyl, oxy-lower-alkyl, silyl-lower-alkyl, phenyl, halo phenyl, alkoxyphenyl, trihalomethyl, dihalomethyl, and similar substituent where lower alkyl has 1 to 6 carbons. The polymerizable oligomers or compounds formed hereby are preferably included in compositions that are dental impression materials for forming impressions.

Materials prepared by treating liquid polysulfide with a synergistic accelerator system comprising a metallic peroxide, e.g., zinc peroxide, 2,2' dithiobisbenzothiazole and 2-mercaptobenzothiazole can also make semi-solid or paste-like elastomeric materials having the capability of precise surface detail reproduction at ambient and body temperature. These dental impression materials are liquid polysulfide polymers, such as, for example, Thiokol LP-2 which is a polymer of bis(ethylene oxy)methane containing disulfide linkage. The polymer segments are terminated with thiol groups. The average structure of the liquid polysulfide or LP-2 polymer is as follows:

HS—(R—S—S)—R—SH, wherein R represents an organic group, $(C_2H_4-O-CH_2-O-C_2H_4)$.

The average molecular weight of the Thiokol LP-2 polymer is approximately 4,000.

In the dental alginate impression materials, the powdery dental alginate impression material made by mixing and kneading powders and water is most widely used. The pasty alginate-based material is also used as an impression material, which is more suitable for this disclosure. The impression compositions consists of two paste components, characterized in that the constituents which change adversely from the use aspect in the presence of water are contained in the anhydrous paste A and the constituents which do not change adversely from the use aspect in the presence of water, and water, are contained in paste B. Constituents such as the alkali metal alginate, calcium sulfate dehydrate, alkali metal phosphate, fluorides and metal oxides are introduced into a paste A and inert fillers are introduced into a paste B. Bases for paste A are glycerol, glycols, olyethylene glycols and polypropylene glycols and mixtures of these in other anhydrous substances. Gel-forming agents are employed in the water-based paste B, on the one hand to prevent sedimentation of the fillers and on the other hand so that, by adjusting viscosity to that of paste A, subsequent easy mixing with this paste is ensured. Such gel-forming agents include but not limited to methylcellulose, hydroxypropylcellulose, hydroxyethylcellulose, carboxymethylcellulose and alkali metal polyacrylates and copolymers.

One embodiment of the dispenser disclosed herein is a pneumatic dispenser 10 that connects to the supply air on the dental chair (not shown). Such a connection is a convenient and economical use of an energy source that is readily available in the dental operatory. The device consists of a pneumatic cylinder 1 and a conical spring 2 for returning the cylinder's piston 3 back to the starting position without the need for complex air control return mechanisms. The amount of air pressure on the cylinder may be from about 200 kPa to about 500 kPa, such as from about 250 kPa to about 450 kPa or from about 300 kPa to about 400 kPa. A forked plunger 4, which is connected to the cylinder's piston 3, acts upon the cartridge pistons 5 which seal the cartridge.

Figure 6:
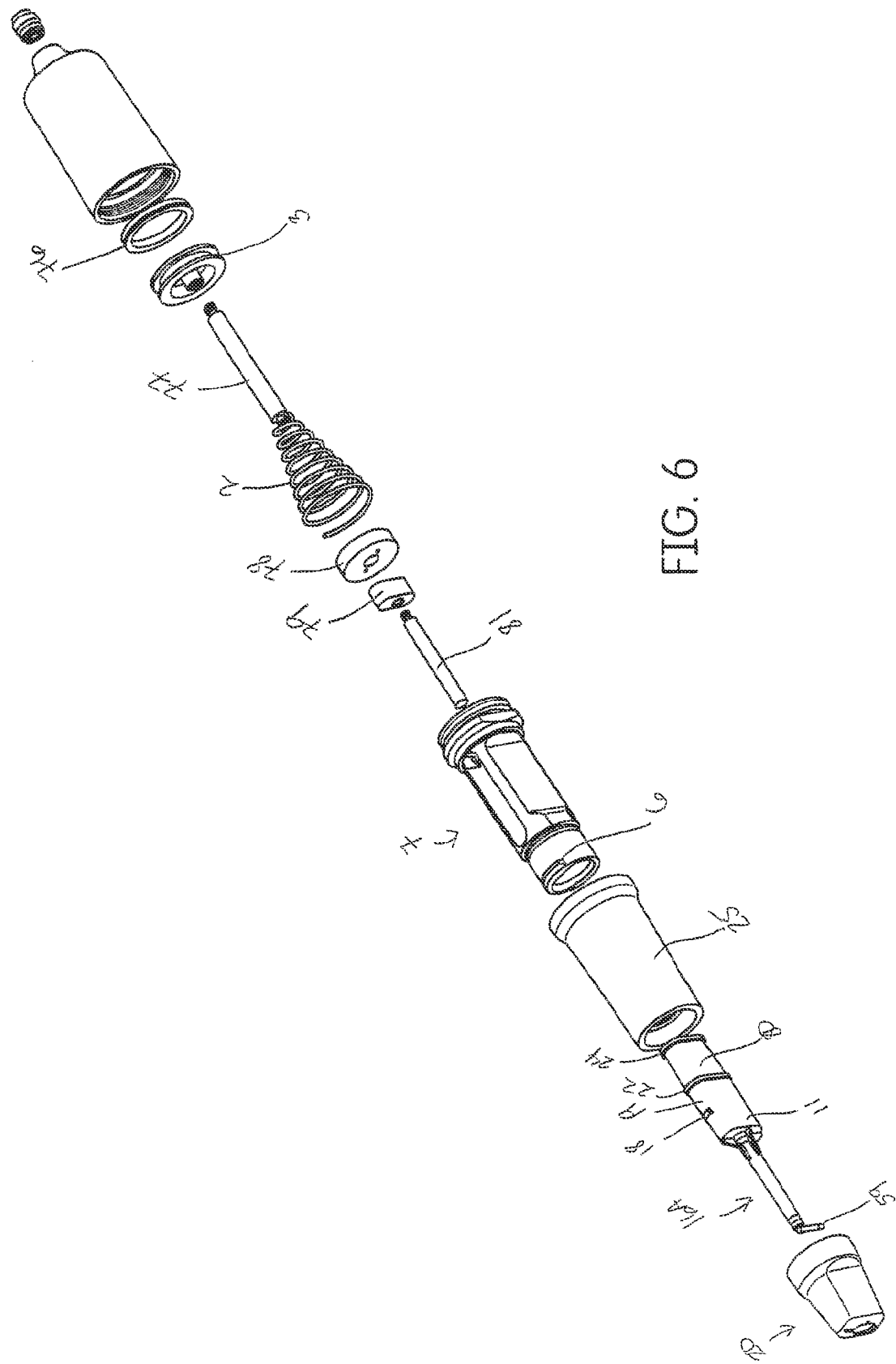
FIG. 6 shows one embodiment of the assembly of FIG. 5 showing a single plunger rod and a single cartridge barrel or a single component material.
Figure 7:
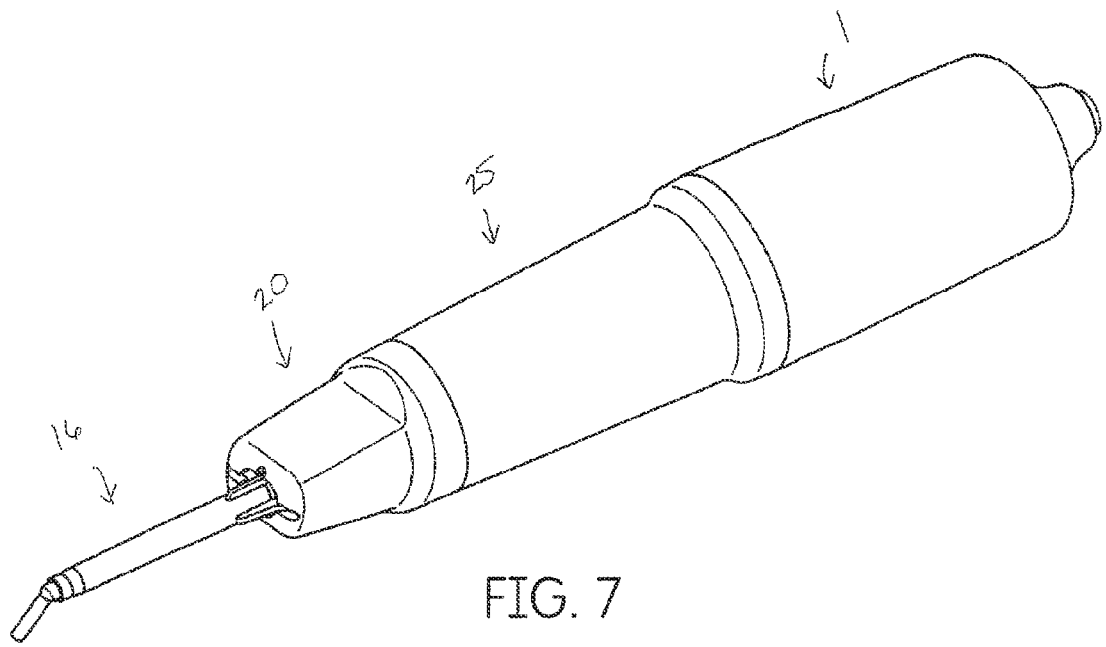
FIG. 7 is an illustration of the dispenser of FIG. 1.
Figure 8:
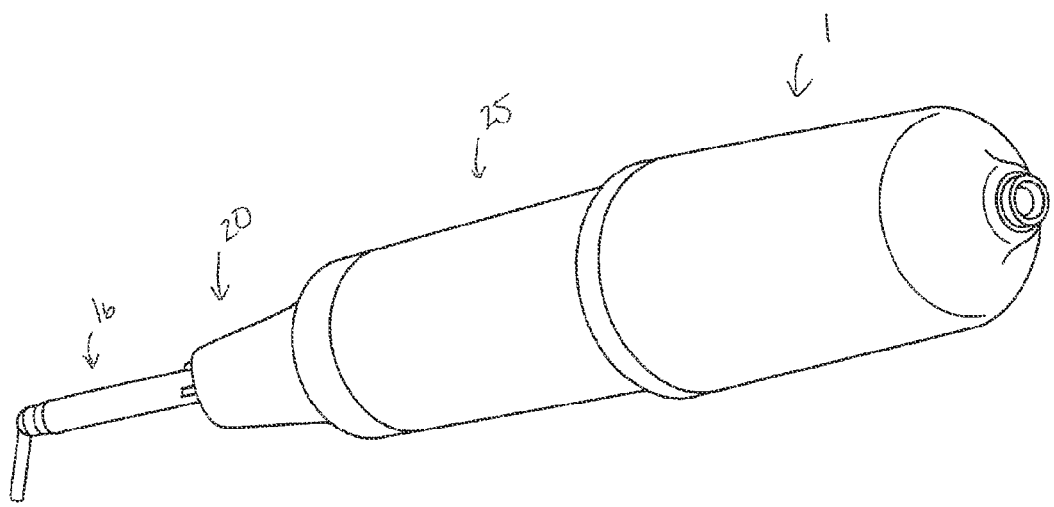
FIG. 8 is an illustration of the dispenser of FIG. 1.

The body of the device has a means for attaching unit dose cartridges similar to those shown in U.S. Pat. No. 8,016,161, which is incorporated herein in its entirety by reference. The body 7 has a bayonet thread 6 for attaching a cartridge retainer cap 20. The top portion of the unit dose cartridge (the portion with the mixtip housing) fits inside a pocket 9 inside the retainer cap 20. The mixing tip or mixtip 16 includes the mixing housing 11 and the mixer 83 therein. The pocket 9 fits intimately with the mixtip housing 11 and secures the cartridge 15 inside the retainer cap 20. The cartridge 15 has a shoulder 12 which fits into an undercut 13 in the mixtip 16 and the mixtip 16 fits intimately within the retainer cap 20. This assembly structure secures the cartridge shoulder 12 within the mixtip undercut 13 and counteracts the forces which would otherwise cause the cartridge 15 to dislocate from its position in the mixtip 16 due to the high pressure required to extrude the material. In one specific dispenser assembly, the dispenser may include an O-ring 76, a plunger rod 77, and a connector 79 for connecting the plunger rod 77 to the forked plunger rod 4. As will be understood by one of ordinary skill, the forked plunger rod 4 is necessary when the dispenser include a dual barrel cartridge as shown in FIG. 5. In an alternative embodiment, when the dispenser includes a single barrel cartridge 80, then a single bodied plunger rod 81 may be used instead of a forked plunger rod. See FIG. 6. The plunger rod 77 is then optional and may be connected to the single bodied plunger rod 81 via a connector 79 for the plunger rod. Or the single bodied plunger rod 81 may be formed integrally (not shown) such that the piston acts directly on the single bodied plunger rod 81 with the need for the plunger rod 77 and the connector 79 for the plunger rod. In the embodiment of FIG. 6, the mixing tip may be substituted with an extrusion tip 16A as the dental material may not need to be mixed prior to extrusion. Such an extrusion tip 16A is similar to the mixing tip 16 of other embodiments except that a mixer 83 inside the mixing tip 16 is not necessary.

The cartridge 15 also has spurs 17 that fit into square holes 18 in the mixtip 16. The mixtip housing 11 below the spur 17 is similarly supported by the retainer cap 20 through an intimate fit to counteract the deformation that would occur under high pressure and otherwise cause the cartridge 15 body to dislodge from the mixtip 16.

The body 7 of the pneumatic dispenser has an upper ledge 21 that abuts the bottom of the first cartridge flange 22 when the retainer cap 20 is secured to the body 7 using the bayonet thread 6. This ledge further backs up the cartridge and prevents the cartridge from dislocating from the mixtip under extreme pressure. Effectively, the cartridge is clamped in place from the assembly of the cartridge, mixtip, retainer cap and dispenser body.

A second cartridge 23 with an extension 28 beyond the previously mentioned first cartridge flange 22 can be utilized within the same dispenser to deliver a larger volume of material. The extension 28 has a second end flange 24 with the same oval profile as the first abutment flange 22. A cartridge 23 with an extension 28 is inserted into a retainer cap 20 in the same way previously described, except the extension 28 protrudes outwardly away from the retainer cap 20. Once loaded into the retainer cap 20, the extension 28 portion of the cartridge is inserted into the opening in the dispenser body 7 until a location 29 at the lower end of the retainer cap 20 meets the outer sleeve 25 of the dispenser, thereby positioning the bayonet thread 6 in locking position. At this point the first flange 22 is also abutted by the ledge 21. Upon rotation of the bayonet thread 6, the end flange 24 rotates under an undercut 83 in the supporting ledge that forms the abutment surface. Upon rotating approximately 90° the outside chamber side wall 26 of the extension contacts an end wall surface 27 of the ledge and stops the rotation. Upon stopping, the cartridge chambers are properly aligned with the piston rods of the forked plunger 4. This configuration permits the cartridge extension 28 to be variable in length and suitable for various cartridge volumes depending on the product application.

The upper ledge 21 has a chamfer 30 that leads to the top surface of the ledge. The chamfer 30 acts as a ramp to drive the first flange 22 of the cartridge mixtip assembly forward into the retainer cap 20, if it is not already fully seated.

The clearance opening 31 in the dispenser body through which the cartridge extension flange fits, is oriented 90° to the forked plunger 4 before rotation of the retainer cap 20.

The aforementioned cartridge locking and alignment assembly method is a unique and novel feature of this disclosure. It works equally well with cartridges with extensions or without. Another benefit of this construction and assembly method, where the cartridge is rotated into position, is that the cap can be constructed from one piece and therefore reduce manufacturing costs.

Figure 10:
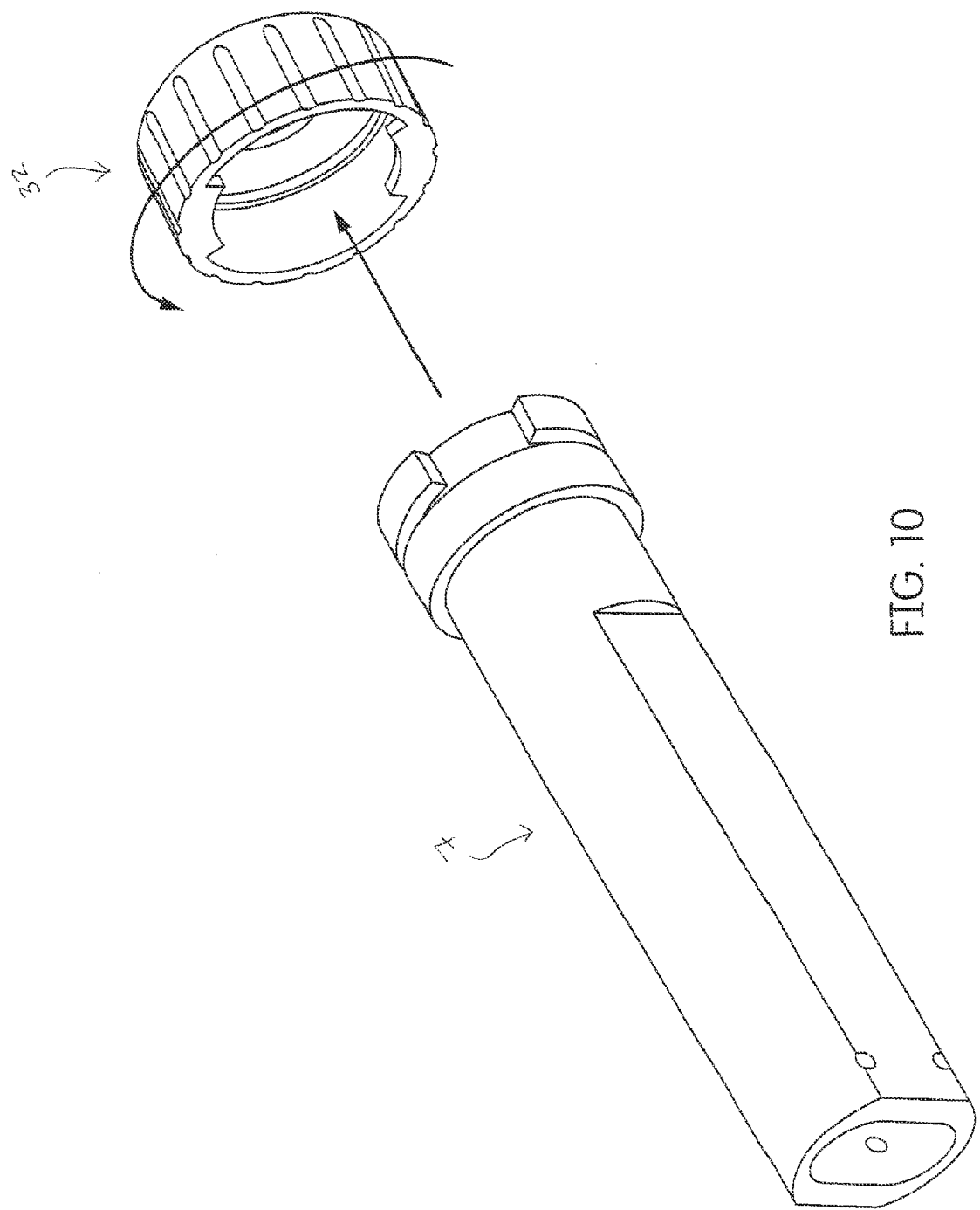
FIG. 10 demonstrates one embodiment of a bayonet cap of FIG. 9.

Another embodiment of the retainer cap 20 is depicted in FIG. 10. In this embodiment the cartridge is oriented with the plunger rods and does not rotate. The bayonet cap 32 contains a rotating member that allows the orientation of the cartridge chambers to remain stationary, while the bayonet cap 32 rotates.

Figure 9:
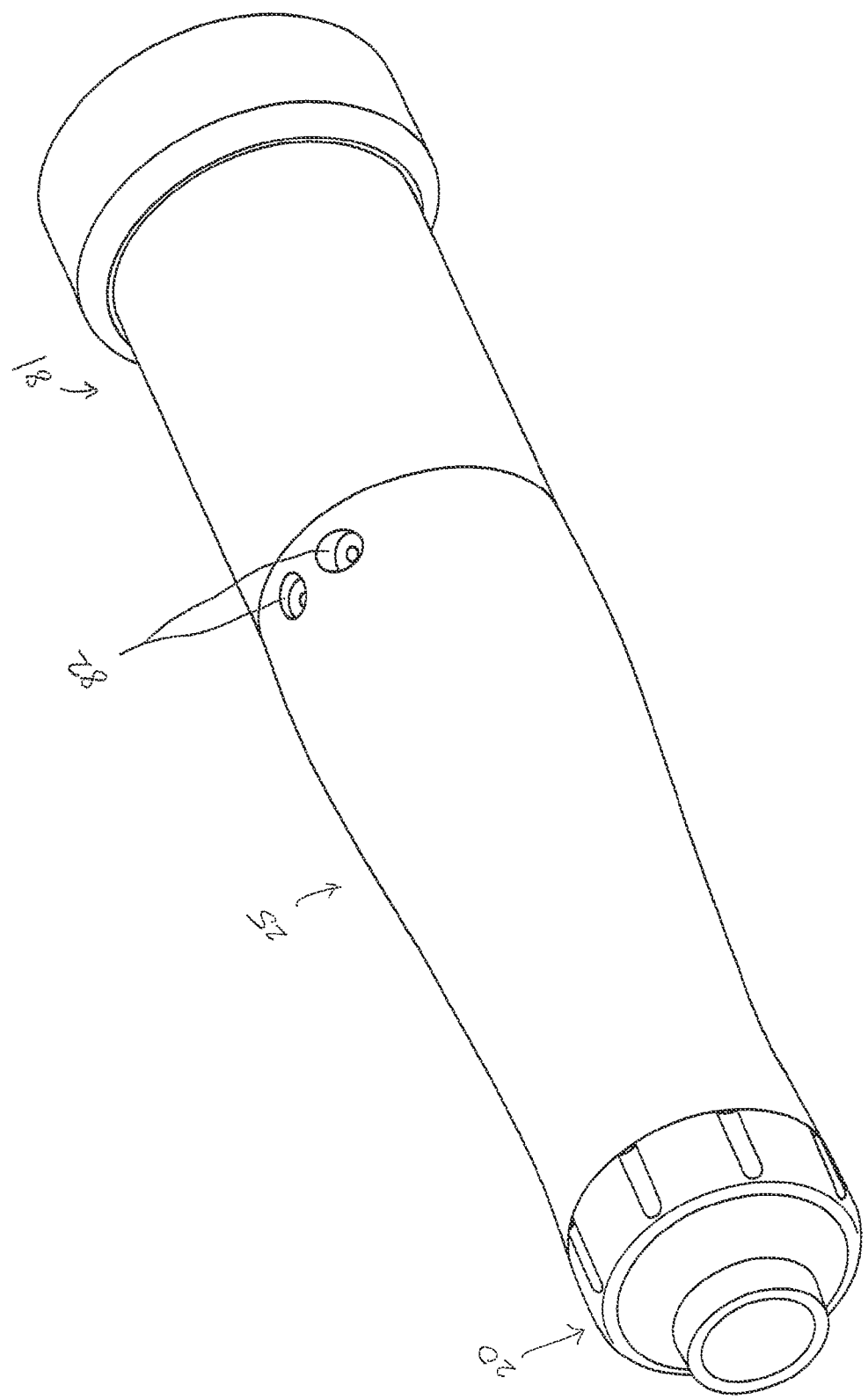
FIG. 9 is an illustration of one embodiment of a dispenser of FIG. 1.

FIGS. 7, 8, 9 and 11 demonstrate various possible tissue management impression material dispenser embodiments that may be suitable. For example, FIG. 9 depicts one embodiment of a wireless dispenser that includes ports 82 for charging. These ports 82 could be placed in any suitable location on the dispensing device so long as the device is capable of being charged. The various embodiments of FIGS. 7, 8, 9 and 11 may also depict various possible retaining caps 20 and various suitable inter oral tips. It is understood that each of these features is an example and could be modified as necessary.

Figure 12:
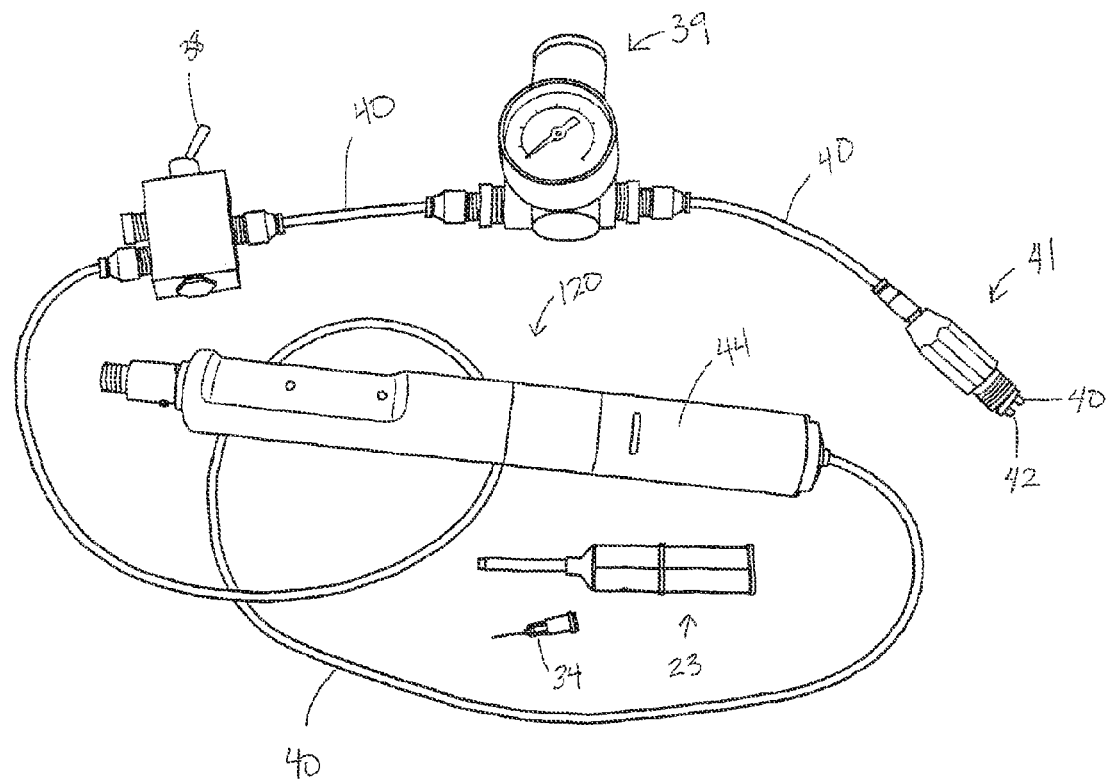
FIG. 12 shows one embodiment of a dispenser for a tissue management impression material disclosed herein.
Figure 13:
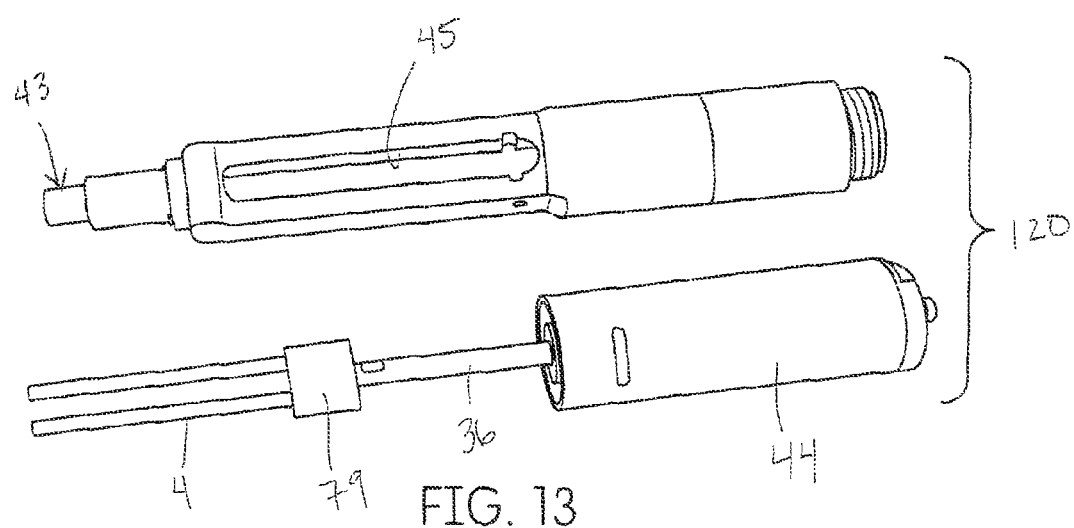
FIG. 13 demonstrates the assembly of the dispenser of FIG. 12.
Figure 14:
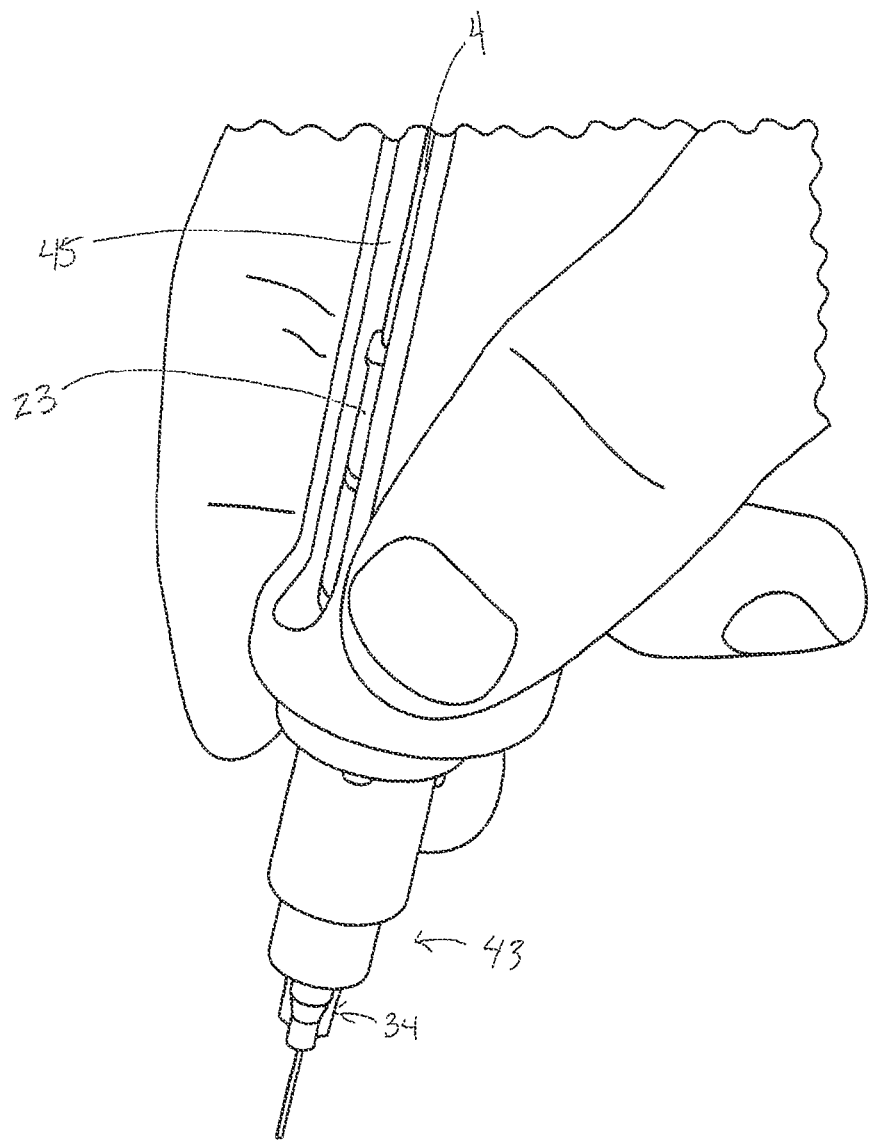
FIG. 14 demonstrates how a user would hold a dispenser of FIG. 12.

Another embodiment of the pneumatic dispenser is shown in FIGS. 12-14. This device is configured to use the same cartridge and mixtip system but has a breach 45 (side) loading and luer 43 threaded applicator tips 34. As depicted in FIG. 12 the device is connected to an air supply tube 40 for pressurizing an air cylinder 44 that drives a plunger rod 36 connected to a forked plunger rod 4. The tube is connected to an on/off switch 38 then a pressure regulator 39 and finally a threaded ISO 4-hole connector 41 for attachment to the dental chair tubing on the dental delivery unit. FIG. 13 depicts and unassembled pneumatic device 120.

Figure 11:
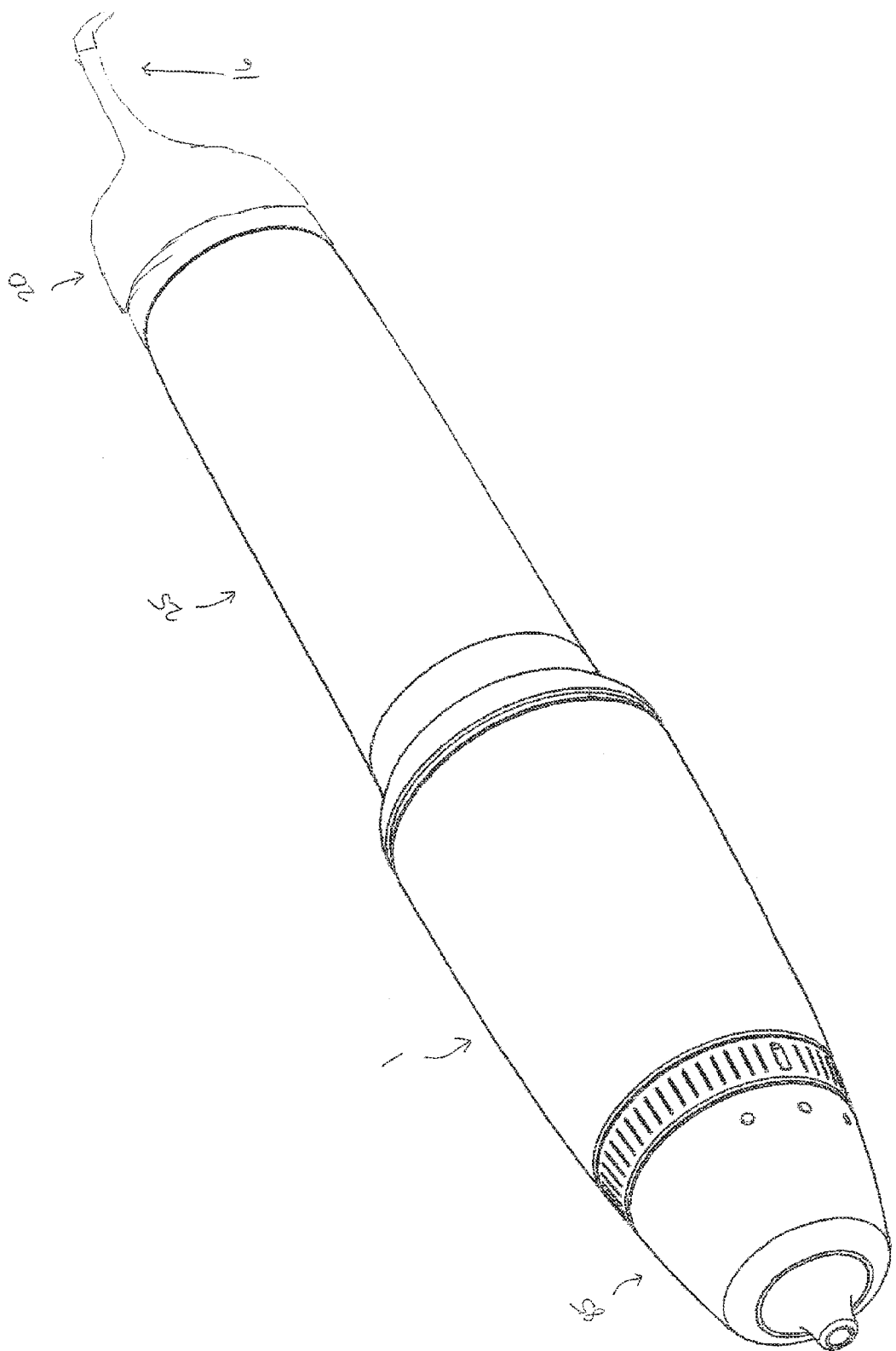
FIG. 11 is an illustration of one embodiment of a dispenser of FIG. 1.

In another embodiment, the regulator 39 and on/off switch 38 can be incorporated 85 into the dispenser handpiece itself as shown in FIG. 11.

The ISO 4-hole connector 41 only has fittings for air supply 40 and exhaust 42 (electric and water have been terminated in this connector). Inside the ISO connector, a vent hole, preferably 0.018 inches in diameter, connects the supply air line to the exhaust air line. The vent allows the air to bleed from the system after activation and permit the plungers to retract to the starting position. This vent is particularly necessary with dental chairs with electrically operated foot switches that are frequently used in Europe (most dental chairs in the US have air operated foot switches which bleed supply air to exhaust). Without the vent and on a chair with an electric foot switch, the plungers would stay locked in a forward position and the operator would not be able to stop the flow by un-depressing the footswitch. Vents with diameters of 0.025, 0.036 and 0.052 inches have also been utilized to yield adequate results.

Other devices may be used to extrude the tissue management impression material disclosed herein into the sulcus. Examples of suitable devices include manual dispensers, spring loaded dispensers, mechanical dispensers, battery operated motorized dispensers, electric motorized dispensers, compressed gas cartridge dispensers and pneumatic dispensers. While many types of dispensers may be conceived, it is necessary that the dispenser evenly and accurately be capable of extruding small amounts of the tissue management impression material into the sulcus of a patient. In embodiments, the dispenser is capable of extruding extremely small amounts of the tissue management impression material, such as less than 2 grams, or less than 1.5 grams or less than 1 gram, or less than 0.5 gram into the entire sulcus per prepared tooth of a patient. In order to accurately extrude such small amounts of viscous tissue management impression material, the dispenser must provide ample pressure and be of sufficient strength to consistently extrude and accurately place the tissue management impression material into the sulcus of a patient. The amount of pressure on the tissue management impression material in the cartridge may be from about 2600 kPa to about 5000 kPa, such as from about 3000 kPa to about 4500 kPa or from about 3500 kPa to about 4000 kPa.

In addition, the device should alleviate the dentist from exerting physical strength to extrude the material so that he may focus entirely on precise placement of the tissue management impression material without the encumbrance of having to simultaneously exert pressure on a dispenser to extrude a material. Anyone practiced in the art will readily see the advantage of not having to simultaneously exert pressure on a dispenser while trying to precisely deliver the material to a small site such as a tooth preparation. In addition, the pen-shaped dispenser allows for a more ergonomic delivery which aids precision placement of the material.

Figure 15:
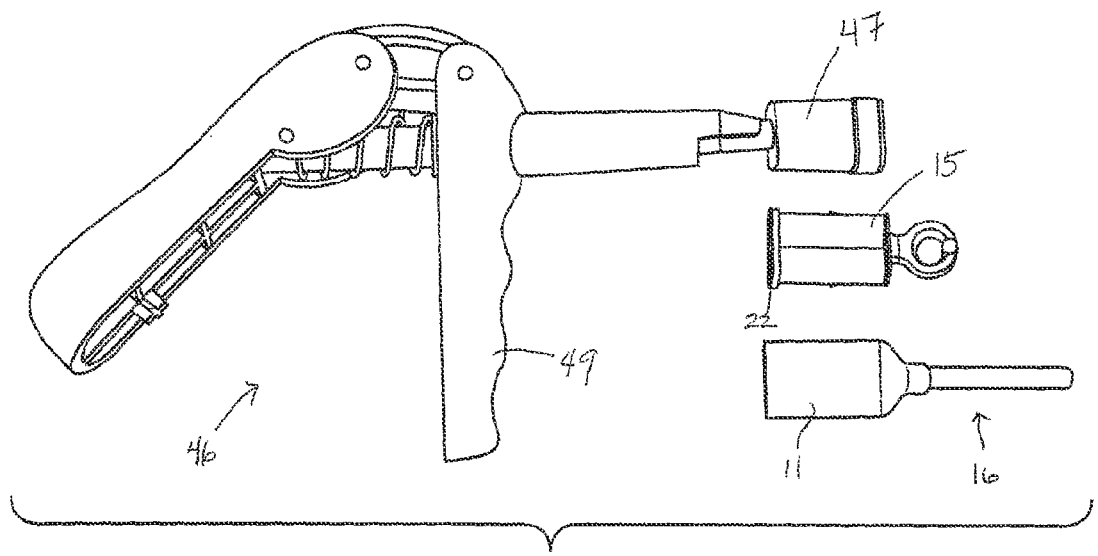
FIG. 15 shows one embodiment of a manual dispenser for a tissue management impression material disclosed herein.
Figure 16:
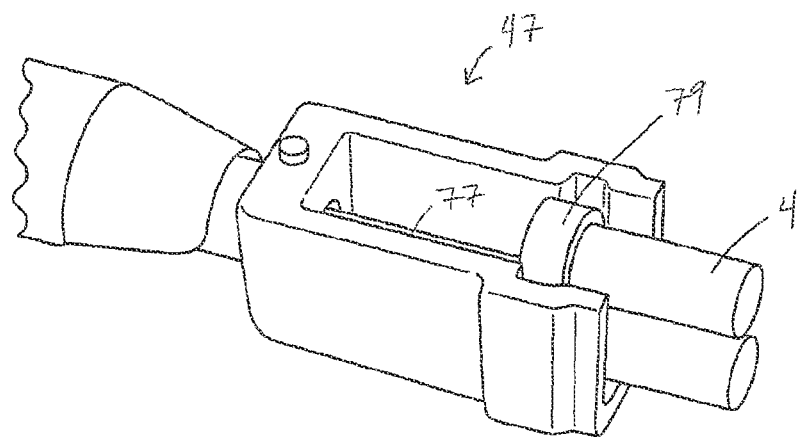
FIG. 16 shows an illustration of the adapter of the manual dispenser of FIG. 15.

One embodiment of a dispenser is a manually powered syringe or gun style dispenser. Such a dispenser would not provide the ergonomic benefit of a powered delivery, but would otherwise be sufficient for delivering materials that would not require such precision placement. The manual dispenser would have a forked plunger 4 that would be activated by manual means. FIGS. 15 and 16 illustrate one embodiment of a hand powered (manual) dispenser 46, such as a typical capsule extruder. In this embodiment a forked adapter 47 is attached to a typical capsule extruder. The adapter 47 holds the dual component cartridge 15 and mixtip 16 and transfers the motion of a single piston rod 77 into a forked piston rod 4. To activate the gun style dispenser 46, the dentist would pull a lever (trigger) 49 to advance the connected plunger rods.

In the case of a syringe style dispenser as described in the Pierson 161 patent, the dentist would press the palm of his hand against a plunger which is tied to a forked plunger rod.

Figure 17:
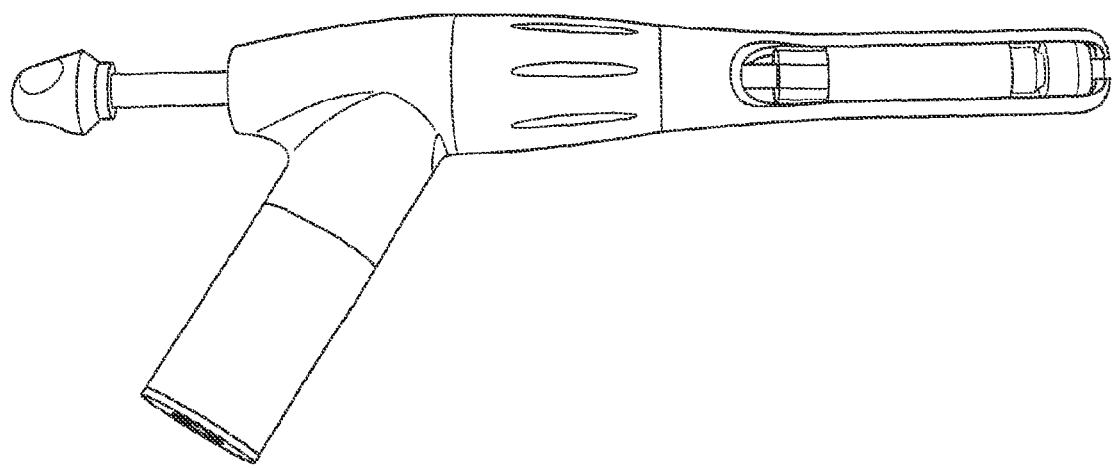
FIG. 17 shows a powered dispenser of prior art for a single component, clay based retraction paste.
Figure 18:
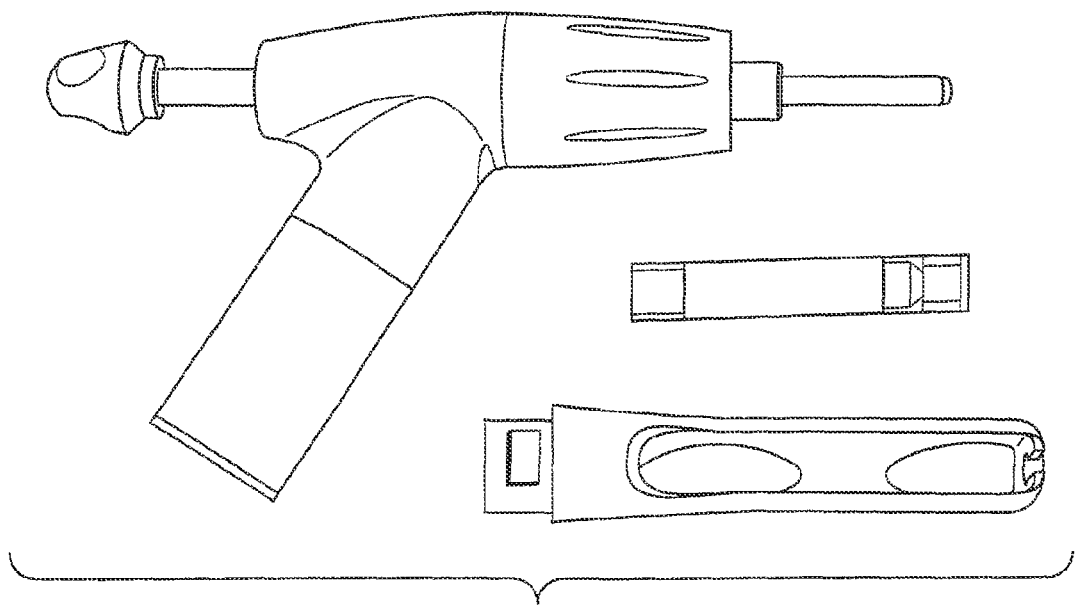
FIG. 18 shows the prior art assembly of the dispenser of FIG. 17.

Another embodiment of a dispenser is a mechanical version which utilizes a dental micro motor or slow speed air turbine as an energy source. FIGS. 17 and 18 depict prior art which has been used for dispensing clay based retraction material. Similarly, a mechanically driven device could be configured with two plungers and adapted to hold the dual component cartridges of tissue management impression material disclosed herein.

Another embodiment of the dispenser is a battery operated motorized device. In this embodiment, the plunger rod would be driven by a motor such as a stepper motor for example. In lieu of being battery operated such a device could be electrically powered with a power cord and motor driven by a 120 V electric source, for example.

All of the manual, mechanical and pneumatic dispensers aforementioned, except the manual syringe dispenser, are designed to provide a mechanical advantage when expressing the tissue management impression material. The mechanical advantage is advantageous because the thin gauge applicator tip necessary for inter sulcular placement increases the extrusion force to a point where mechanical assistance can be appreciated.

In embodiments, after the tissue management impression material has been placed in the sulcus and before it cures, a tray of impression material may be inserted to capture the tissue management impression material in the final impression. The materials cure in the mouth and are removed. The tissue management impression material reproduces the dental margin in the final impression that is necessary for crown fabrication. Ideally, the tissue management impression material has sufficient tear strength and preproduction detail to record the dental anatomy in a final impression.

In one embodiment, the filled unit dose cartridge may include two barrels for two different materials. For example, one barrel may include a base material while the other barrel may include a catalyst material. As the base material and the catalyst material are extruded, they will react to form a tissue management impression material.

Figure 19:
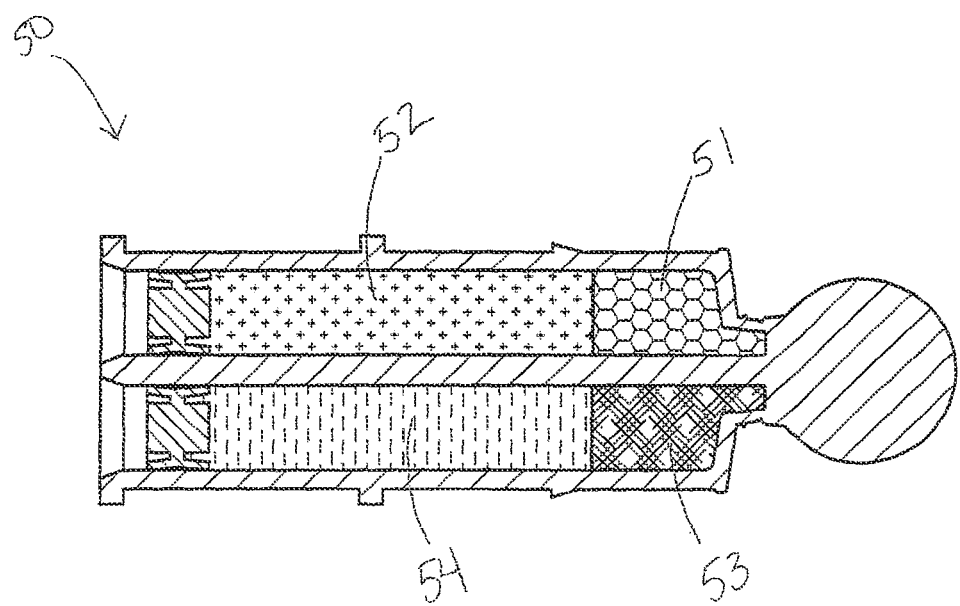
FIG. 19 demonstrates a cartridge filled with layered product suitable for dispensing multiple phases of tissue management impression material disclosed herein.
Figure 20:
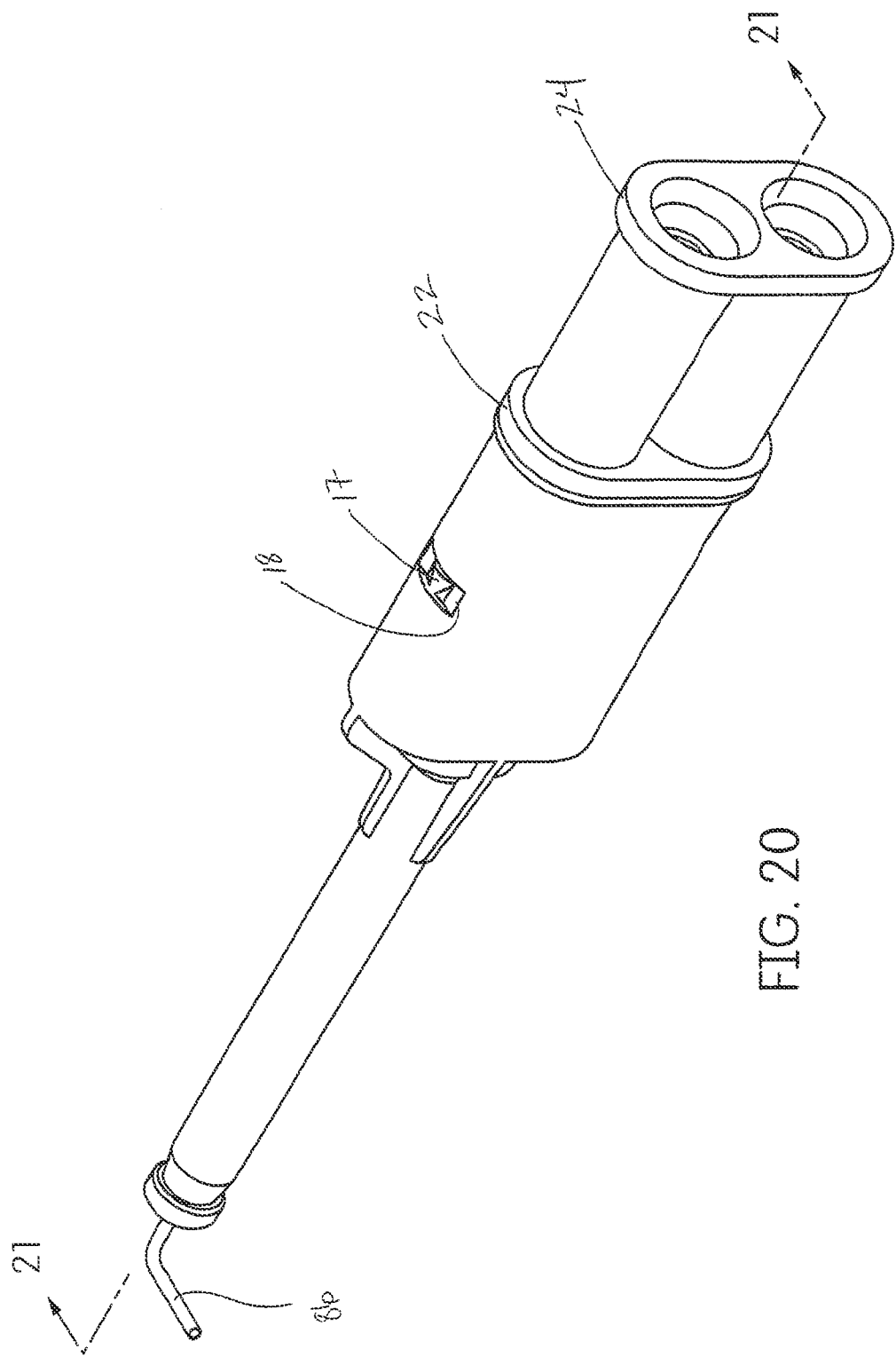
FIG. 20 shows one embodiment of a cartridge, mixtip and inter oral delivery tip subassembly for a tissue management impression material disclosed herein.
Figure 21:
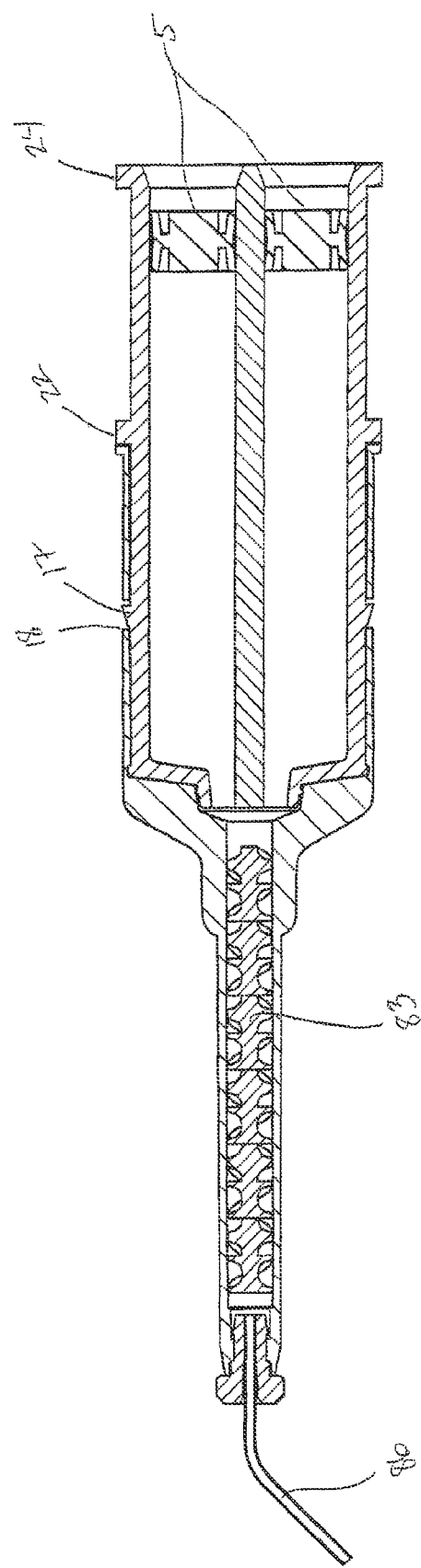
FIG. 21 shows a cross section of the subassembly of FIG. 20.

One alternative embodiment of this disclosure is to use a filled unit dose cartridge 50 that is layered with the aforementioned tissue management impression material followed by a layer of thinner viscosity wash material. The layering is depicted in FIG. 19. One side of the cartridge would contain the two catalyst materials 53 and 54 and the other side would contain the base materials 51 and 52. The increment materials 51 and 53, one base and one catalyst which form the tissue management impression material, that would come out first could be a specifically designed tissue management impression material with handling and flowability characteristics desirable for use in the sulcus. The following material could be a lower viscosity wash material 52 and 54, a base and a catalyst material, for flooding the prep. Each layer of paste (after passing through the mixtip), would have different and distinct colors and flow characteristics. In use, the tissue management impression material would be placed in the sulcus, when the material exiting the tip changes color, indicating the next layer is coming out, the practitioner would begin flooding the prep like they normally would. The wash material 52 and 54 would extrude much faster because of its lower viscosity at a point in the procedure when precision is no longer important, but speed is.

The high viscosity tissue management impression material may be selected but not limited to Type 0, 1 or 2 (as defined by ISO 4823) elastomeric impression materials. The lower viscosity material may be selected but not limited to Type 2 or Type 3 (as defined by ISO 4823) elastomeric impression wash materials. Both the tissue management impression materials and the wash materials may be any elastomeric impression material, such as vinylsiloxane, polyether, polyacrylates, polysulfides, alginate, etc., as described more fully above. The tissue management impression material should be compatible with associated elastomeric wash and tray impression materials.

Another embodiment of the layered cartridge is when there is a single catalyst paste and two different base pastes layered as described above or one base paste and two catalyst pastes.

The applicator tips 86 must be sufficiently thin to access the sulcus directly without causing tissue trauma. For example, applicator tips of existing prior art have a canula that is 18 g (about 1.3 mm diameter), which is too large to access the sulcus directly without causing tissue trauma. Clay based retraction pastes commonly have large gauge needles such as 18 g. In embodiments, the applicator tips disclosed herein are 21 g (about 0.8 mm diameter) or 22 g (about 0.7 mm diameter) and thin enough to be placed directly into the sulcus. Canulas from 20 gauge (about 0.9 mm diameter) to 27 gauge (about 0.4 mm diameter) are particularly useful in this procedure because they are small enough to access the sulcus without causing trauma and are wide enough to allow passage of tissue management impression material when under pressure.

Figure 22:
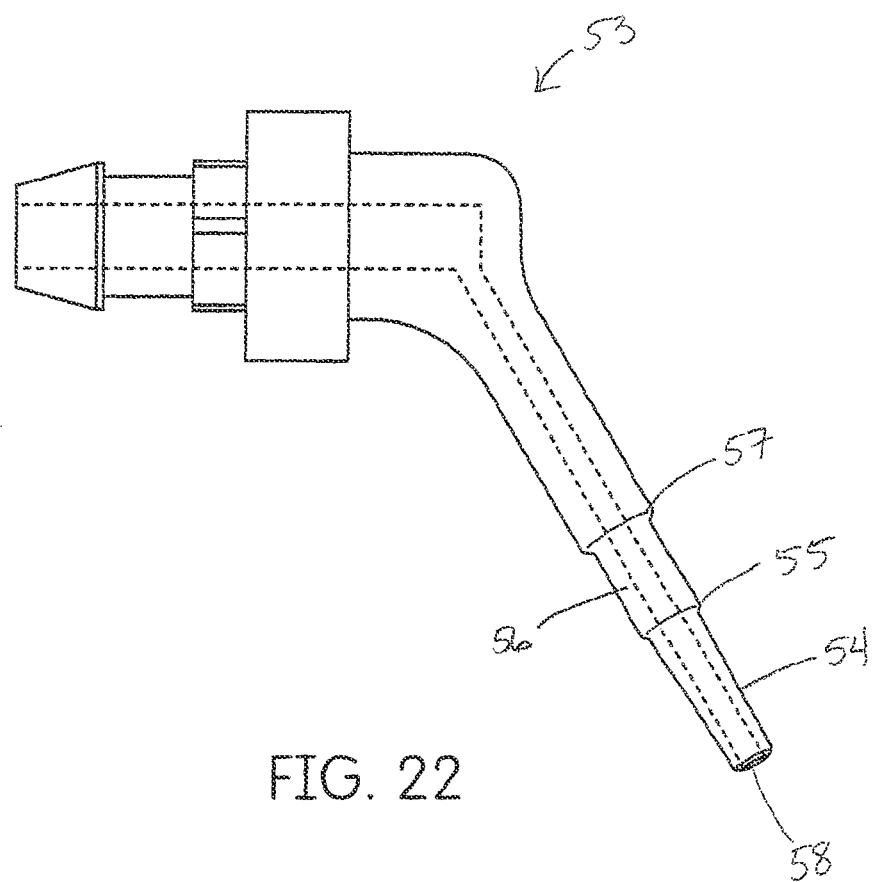
FIG. 22 shows one embodiment of an inter oral delivery tip of FIG. 20.

One embodiment shown in FIG. 22 is a plastic molded tip 53. This tip could be a separate component which attaches to the mixtip as shown or molded as an integral part of the mixtip itself. The molded tip 53 in this embodiment has a narrow section 54 toward the very end of the tip 58 for direct placement in the sulcus. The first step 55 to a wider diameter 56 is positioned from about 2 mm to about 4 mm, such as about 3 mm, from the tip and indicates the depth of penetration to the practitioner. As understood by those skilled in the art, the depth of a healthy sulcus is about 3 mm. The next step 57 is from about 1 mm to about 3 mm, or about 2 mm, further up from the end and is also for the benefit of the practitioner in maintaining visual access and knowledge of tip penetration. In other words, the next step 57 is from about 3 mm to about 7 mm, or from about 4 mm to about 6 mm, from the tip end 58.

Figure 23:
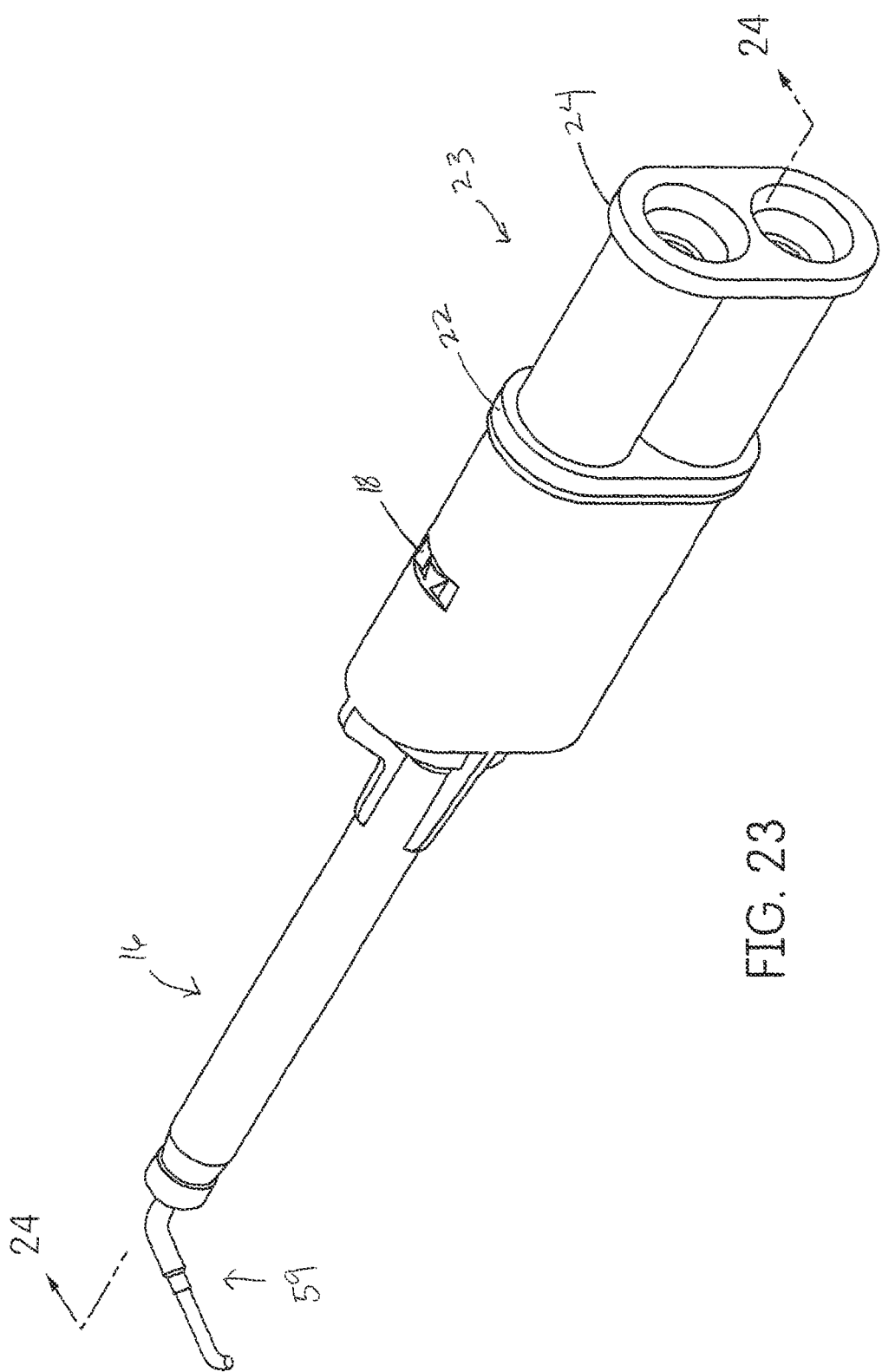
FIG. 23 shows another embodiment of a cartridge, mixtip and inter oral delivery tip subassembly for a tissue management impression material disclosed herein. The inter oral
Figure 24:
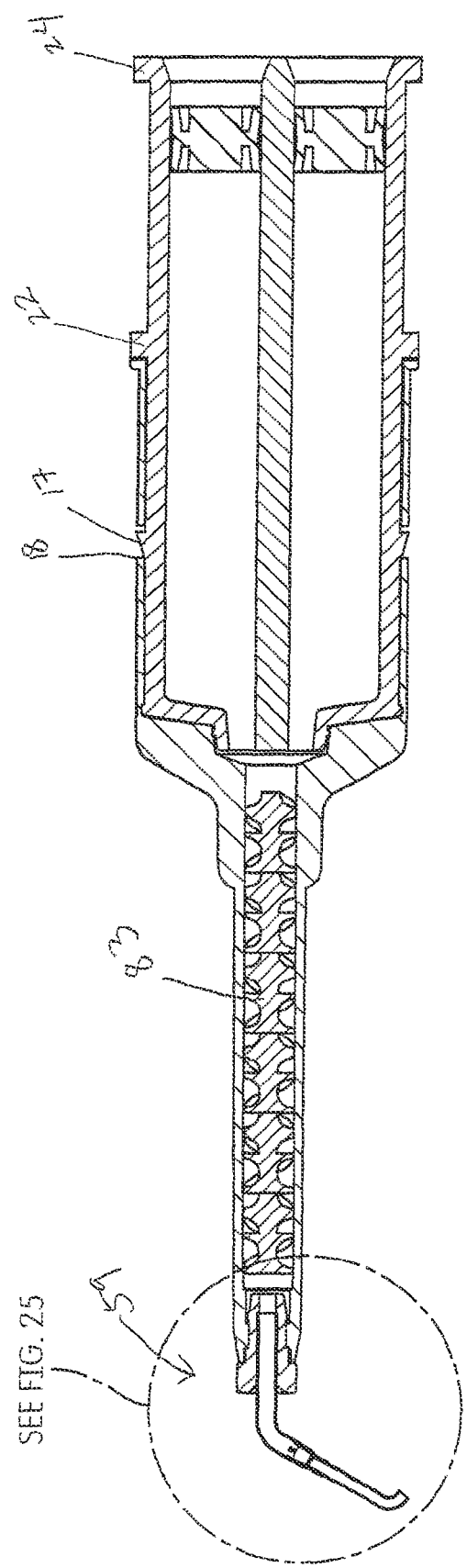
FIG. 24 shows a cross section of the subassembly of FIG. 23.
Figure 25:
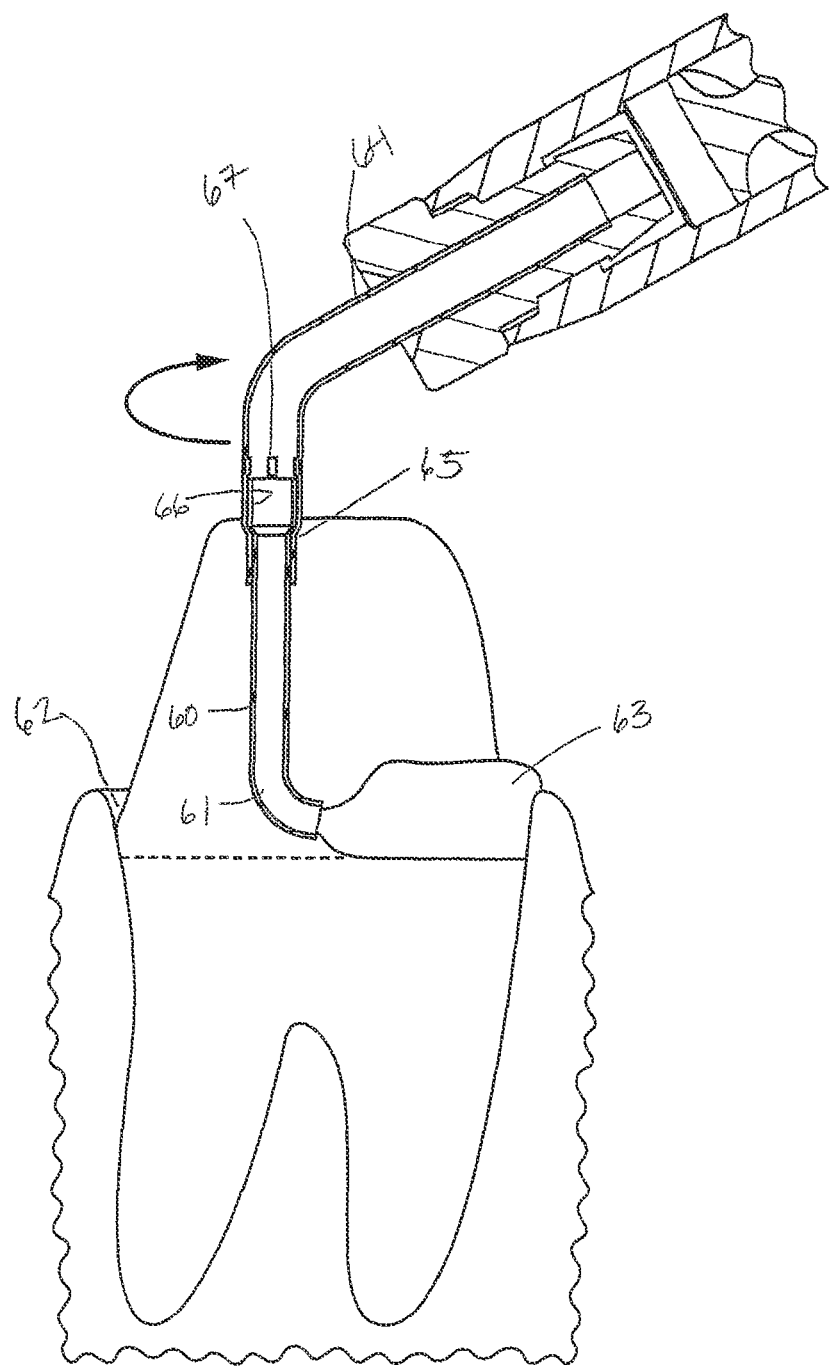
FIG. 25 is a detailed view of the embodiment of the inter oral tip of FIG. 24, shown in relation to the dental anatomy and the deposition of the tissue management impression material disclosed herein.

One embodiment of this disclosure is to utilize an inter oral tip 59 that swivels (rotates) about an axis. The axis is transverse to the axis of the main body of the dispenser, cartridge and mixtip. The angle of the transverse axis is up to 90° but preferably around 30°, 40° or 45°. One such tip is shown in FIGS. 23-25. The portion that swivels is a J-shaped tube 60. The curved edge 61 of the J is the leading edge and can be used to insert the tip into the sulcus 62 without damage or trauma to the tissue. As the practitioner moves the tip around the sulcus the tip self orients itself to the sulcus and deposits the tissue management impression material 63 behind the direction of travel. This improves visibility for the practitioner because he can maintain visual access with the curved or leading edge 61, confirming that the tip 59 is sub gingival throughout application. The swivel is constructed as a tube which fits loosely within an outer tube 64. The outer tube 64 is crimped over the inner tube 60 and detents 67 are embossed above a flare 66 in the inner tube 60 to prevent the inner tube 60 from being displaced. The crimps 65 are such that they capture the inner tube 60 within the outer tube 64 while maintaining a loosely fitting connection to provide the rotation.

Figure 26:
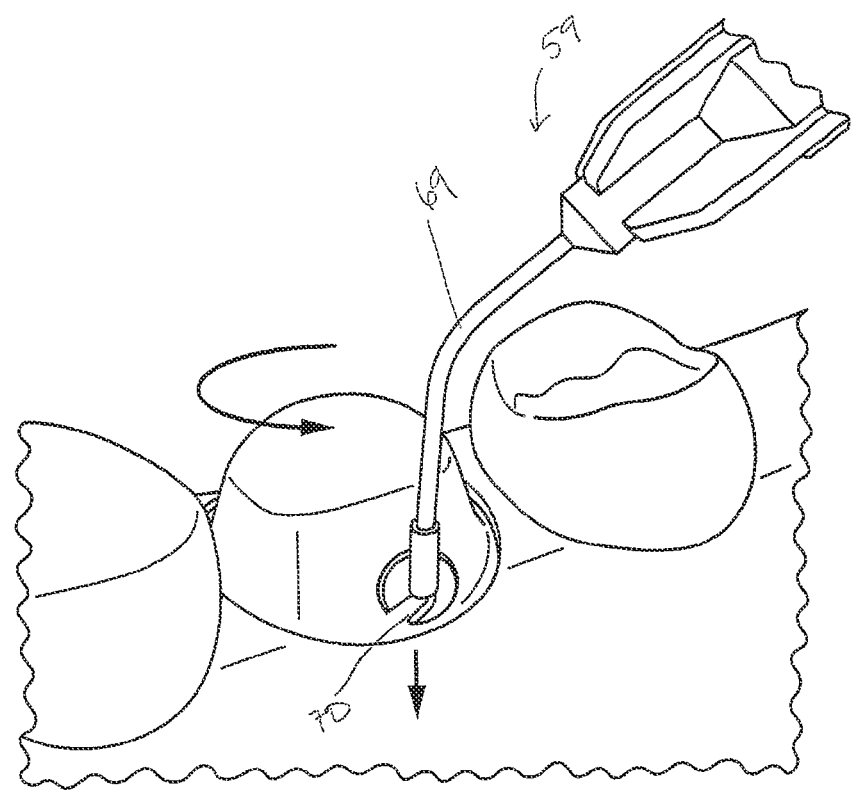
FIG. 26 is another embodiment of a rotating inter oral delivery tip.
Figure 27:
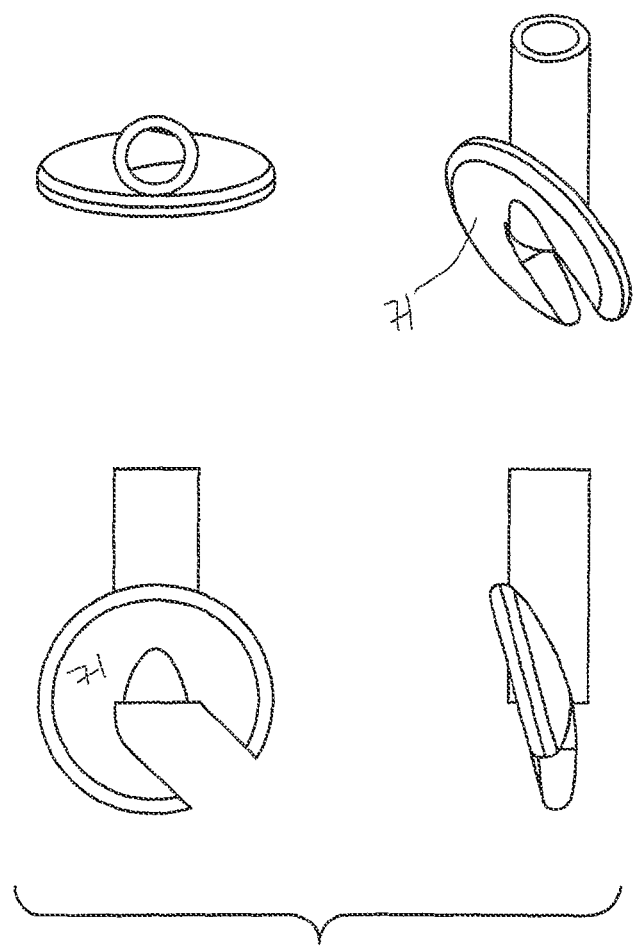
FIG. 27 is series of views of the rotating inter oral tip of FIG. 26.

Another embodiment of the swivel application tip 59 is shown in FIGS. 26 and 27. A small disc-shaped appendage 68 is placed on the end of the injection canula 69. The dish shaped side 71 of the appendage would be oriented towards the tooth and has a channel 70 that directs the material flow behind the direction of travel. The wide and flat shape of the appendage 68 would slip into the sulcus without causing trauma to the tissue and would help maintain directional orientation of the tip as the tip is moved around the sulcus. The appendage 68 would be loosely attached to the canula 69 to permit the appendage 68 to rotate (swivel) freely around the end of the canula.

Figure 28:
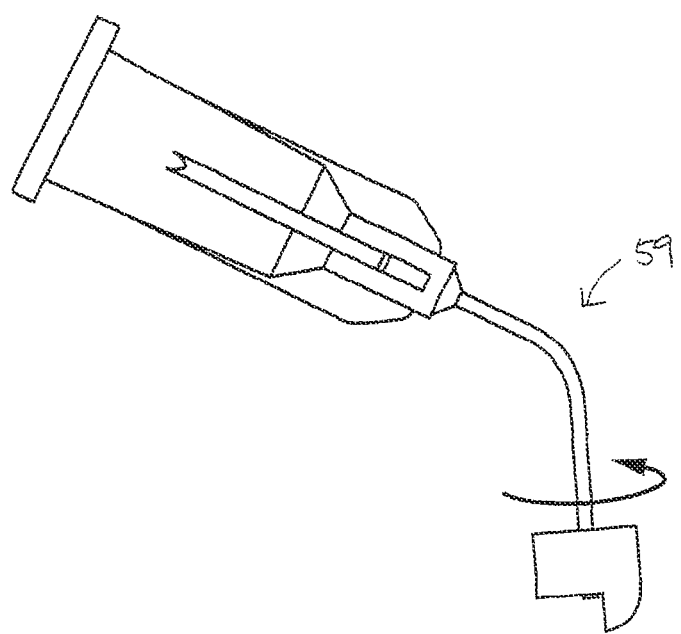
FIG. 28 is another embodiment of a rotating inter oral delivery tip.

Yet another embodiment of the swivel applicator tip is depicted in FIG. 28.

Figure 29:
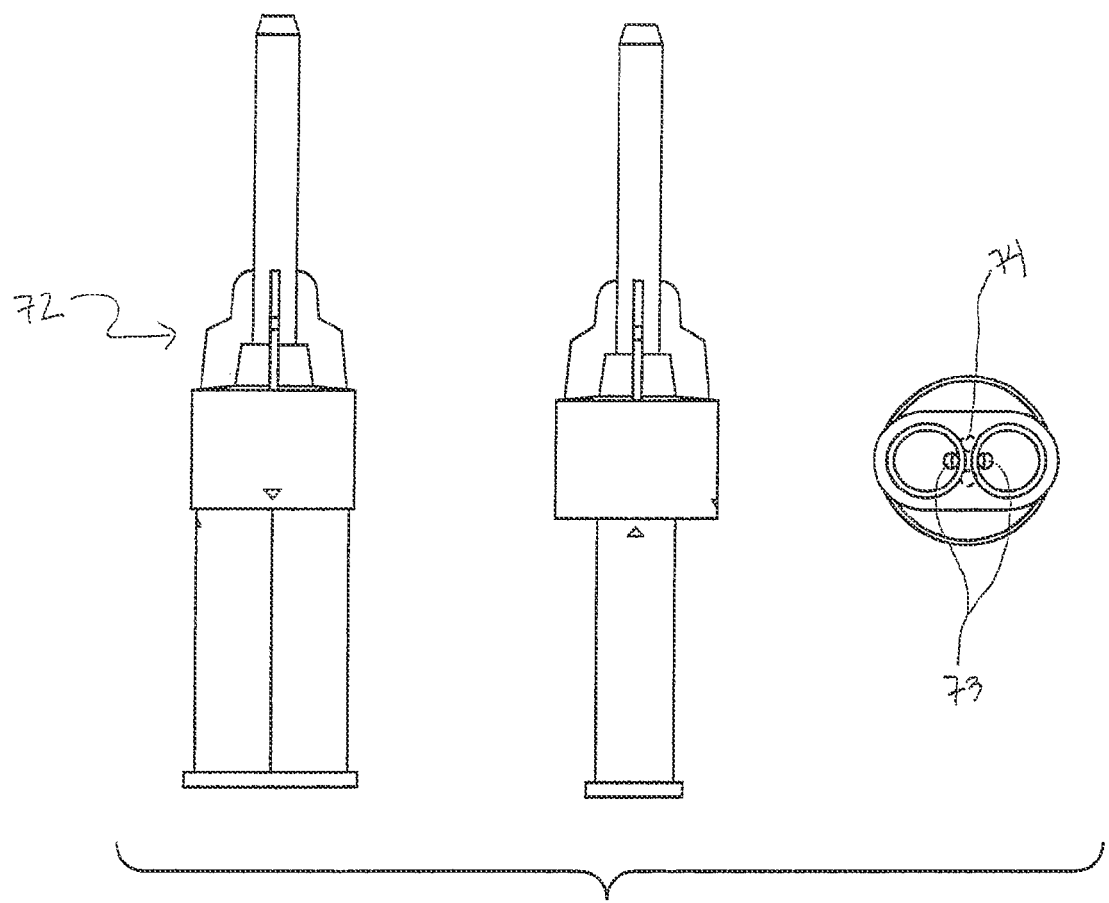
FIG. 29 is one embodiment of a cartridge and mixtip subassembly for tissue management impression material disclosed herein. The cartridge and mixtip are in a closed position as indicated by the misalignment of the triangles.
Figure 30:
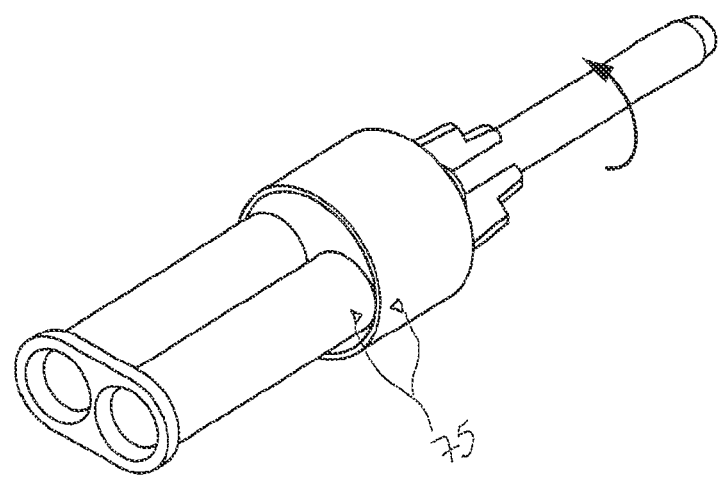
FIG. 30 is an illustration of the cartridge subassembly of FIG. 29 wherein the mixtip has been rotated to an open position for dispensing as indicated by the alignment of the triangles.

Another embodiment of the cartridge is directed to the connection and activation of a cartridge and mixtip, which are integrally formed 72. A cartridge having such a mixtip is demonstrated in FIGS. 29 and 30. A user would rotate the mixtip a partial turn, for example, about 90°, which would simultaneously bring openings 73 in the cartridge body into alignment with openings 74 in the mixtip housing to permit the passage of the materials. To ensure proper alignment, both the mixtip and cartridge may include indicators 75 that match-up or otherwise indicate that the mixtip and cartridge have properly aligned. Such indicators 75 may be arrows, a colored demarcation or any suitable marking that would indicate proper alignment to the user. In another embodiment, twisting the mixtip housing would lift plugs out of the exit ports through a screw mechanism internal to the mixtip housing, which would then open the exit ports to a passageway leading to a static mixer.

In yet another embodiment, an impression pre-treatment material with a hemostatic agent and a wetting agent is applied to the prepared tooth prior to the application of the tissue management impression material to improve subgingival adaptation and bonding of the tissue management impression material and tray material interface. A comparative pre-treatment wetting agent is described in U.S. Publication No. 2007/0184410, but without the hemostatic agent.

Any suitable process for placing the tissue management impression material into the sulcus of a patient may be used. One example of such a process is to first prepare the tooth for a dental impression. Preparing the tooth to receive a crown involves reduction of sufficient tooth volume to allow for the permanent crown to be fabricated. This process routinely involves removing the enamel and some of the dentinal structure to provide axial wall and coronal tooth reduction to coincide with the requirements for the restorative material prescribed for the final restoration. The junction of the tooth to restorative interface is referred to as the margin. The subsequent dental impression must be a defect free negative of the crown preparation and restorative margin as well as the adjacent and opposing unprepared tooth structure. Optionally, a pretreatment solution may be applied to the tooth prior to application of the tissue management impression material or impression material. The pretreatment solution may include a hemostatic agent to control bleeding. Once the tooth has been prepared and any optional pretreatment has taken place, the dental practitioner may insert the inter oral applicator tip into the sulcus of the patient to a depth of about 1 mm to about 3 mm, or about 2 mm. The dental practitioner may then begin to dispense the tissue management impression material into the sulcus. Simultaneously, the dental practitioner may begin to move the tip around the perimeter of the sulcus depositing the tissue management impression material. The dental practitioner may coordinate the flow of material with the speed at which he moves around the prepared tooth so that a uniform and contiguous amount of material is deposited behind the applicator tip in the sulcus of the patient. When the applicator tip has reached the point where application of the tissue management impression material began, the tip may be carefully withdrawn by the dental practitioner and dispensing of the tissue management impression material may be terminated. Optionally, the practitioner may go around the tooth a second time, but outside of the sulcus, building material towards the coronal surface of the preparation. Impression material in a tray is applied to the prepared tooth after the tissue management impression material is applied, but before the tissue management impression material has cured. The materials including both the impression material in the tray and the tissue management impression material in the sulcus will bond together and cure, resulting in a single impression of the tooth that has been prepared for production of a dental device, such as a crown. In other words, the formed impression is composed of both the impression material in the tray and the tissue management impression material in the sulcus.

In an alternative embodiment, an impression may be made by the dental practitioner using a pick-up method. A pickup technique is when the tissue management impression material is dispensed into the sulcus and allowed to fully cure in the mouth before the tray of uncured impression material is seated in the mouth. The uncured tray material is allowed to cure in the mouth and bonds to the cured tissue management impression material, forming a complete final impression. It is important that the interface between the tissue management impression material and the tray material bond together with sufficient strength that they do not delaminate upon removal from a patient's mouth or subsequent use in the dental lab.

The shear strength of the tissue management impression material may be from about 2000 kPa to about 4000 kPa, or from about 2500 kPa to about 3500 kPa or from about 2700 kPa to about 3200 kPa. The shear strength of the tissue management impression material refers to the strength necessary to remove the entire formed final impression from the patient's mouth, including the cured tissue management impression material in the patient's sulcus. This measurement is important in that is describes that the material can be easily removed from the patient's mouth without any deformation or delamination of the final impression.

In embodiments, a light body viscosity wash impression material may optionally be applied to the prepared tooth or the impression tray or to both the prepared tooth and the impression tray. If the light body viscosity wash impression material is applied to the prepared tooth, then such a wash material may be applied to the prepared tooth after the tissue management impression material has been applied to the sulcus of the prepared tooth.

Such a method as described herein requires that the tissue management impression material, once cured, becomes part of the final impression or mold of the prepared tooth that will be used in manufacturing the planned dental device, such as a crown.

IMPRESSION MATERIAL EXAMPLES

Example 1

A two component composition of the present disclosure is formulated in a Base Paste and Catalyst Paste components. Mixing of each component's ingredients is done in a double planetary mixer having a mixing pot heated with circulating water at 45-50° C. and under 65 mm mercury vacuum.

The base paste is prepared by mixing 11.00 parts of a polydimethylsiloxane containing SiH groups, 14.36 parts of a QM resin dispersion in polydimethylsiloxane with terminal vinyl groups (viscosity of 5,000-7,000 cPs), 43.07 parts of a QM resin dispersion in polydimethylsiloxane with terminal vinyl groups (viscosity of 55,000-60,000 cPs), 17.0 parts of crystalline silicone dioxide, 5.0 parts of amorphous silicone dioxide, 5.0 parts of a silanated fumed silicone dioxide, 3.0 parts of Igepal surfactant hydrophilizing agent, and 1.57 parts of colored pigments. All ingredients are combined in a pot by mixing to give a homogeneous base paste.

The catalyst paste is prepared by mixing 28.44 parts of a QM resin dispersion in polydimethylsiloxane with terminal vinyl groups (viscosity of 5,000-7,000 cPs), 42.64 parts of a QM resin dispersion in polydimethylsiloxane with terminal vinyl groups (viscosity of 55,000-60,000 cPs), 17.19 parts of crystalline silicone dioxide, 4.95 parts of amorphous silicone dioxide, 4.95 parts of a silanated fumed silicone dioxide, 0.07 parts of colored pigments, 0.49 parts of plasticizer, 1.13 parts of a solution of an organoplatinum catalyst complex comprising 2.0 wt % platinum in a polydimethylsiloxane with terminal vinyl groups, 0.07 parts of 1,3-divinyldimethyldisiloxane, and 0.16 parts of finely divided platinum metal on Calcium Carbonate.

10 gram base paste and 10 gram catalyst paste are mixed completely. After some minutes, a rubbery-elastic mass is obtained. The viscosity of the mixed pastes is determined in accordance with ISO 4823 as 38 mm. The cured impression material has a tear strength of at least 200 psi and a surface contact angle with water of less than about 50° at three minutes formed from the above composition having a work time of 3 minutes.

Example 2

The impression base paste is prepared by mixing 100 g of a polyether with aziridino terminal group (MW 3600) and 5 g of dibutylphthalate, 50 g of diatomaceous earth. Two grams of oleic acid ethanolamide are further added to the material.

The catalyst paste is prepared by mixing together 80 g of dioctylphthalate, 20 g of 2,5-dichlorobenzenesulfonic acid methylester and 16 g of pyrogenic silica.

The two pastes are mixed together in a weight ratio of 4:1, placed on a suitable impression tray and introduced as usual into the mouth. After 5 minutes, the rubber elastic molding is removed from the mouth, without leaving residue between the teeth. The impression obtained has a high reproduction resolution.

Example 3

A dental impression forming composition was compounded by hand mixing the following two formulations separately at ambient conditions.

The base paste is prepared by mixing 52.05 parts of the polymerizable oligomers, 19.52 parts of polypropylene glycol (MW, 4000), 1.04 parts of benzoyl peroxide, 0.06 parts of butylated hydroxy toluene and 27.33 parts of fillers.

The catalyst paste is prepared by mixing 51.08 parts of the polymerizable oligomers, 19.43 parts of polypropylene glycol (MW, 4000), 0.93 parts of dihydroxy ethyl p-toluidine and 27.20 parts of fillers.

The two pastes were mixed at an equal weight ratio by spatulating on a parchment pad for approximately 45 seconds. The material cured to an elastic solid with a shore A hardness of about 55 (ASTM 19, 1984 testing method) in 6 minutes at ambient temperature.

Example 4

A dental impression composition was compounded by hand mixing 12.27 parts of the polymerizable oligomers, 0.88 parts of Alkyl benzyl phthalate, 0.031 parts of camphorquinone, 0.20 parts of 4-ethyldimethylaminobenzoate, 0.025 parts of butylated hydroxy toluene and 9.83 parts of crystobalite fillers, 1.75 parts of fumed silica and 0.035 parts of blue pigment.

The composition was irradiated for 2 minutes with a 500 watt GE Photoflood lamp containing light from the visible light spectrum with the lamp approximately 2 inches from the specimen. The material cured to an elastic solid.

Example 5

A liquid polysulfide polymer base paste is prepared by mixing 0.95 parts of the silicon dioxide colloidal, 75.72 parts of LP-2 Thiokol liquid polymer, 0.14 parts of clove oil, 17.04 parts of zinc sulfide and 6.15 parts of magnesium trisilicate.

The catalyst paste is prepared by mixing 10.29 parts of 2,2' dithiobisbenzothiazole containing 1.33% free 2-mercaptobenzothiazole, 0.67 parts of purified 2-mercaptobenzothiazole, 22.80 parts of 2-ethylhexyl diphenyl phosphate, 7.42 parts of ethyl oleate, 47.72 parts Zinc peroxide, 0.65 of silicon dioxide and 0.32 parts of colorant.

When an equal volume of the base and catalyst pastes are mixed together, a stable elastomeric impression material is formed in about 7 minutes at room temperature.

Example 6

Paste A: 14.0 parts of calcium sulfate dehydrate, 5.0 parts of magnesium oxide, 19.0 parts of sodium alginate, 1.5 parts of tetrasodium pyrophosphate, 3.5 parts of potassium fluorotitanate and 1 part of colored pigment are ground with one another in a bead mill. 40 parts of polyethylene glycol having an average molecular weight of 400 are initially introduced into a planetary mixer and are mixed with the abovementioned powder mixture to form a homogeneous paste. 16.5 parts of the polyethylene glycol are then added and incorporated. The paste is prepared in the absence of moisture.

Paste B: 0.5 part of HOSTACERIN PN 73 (Hoechst) and 2.5 parts of diatomaceous earth are premixed. This premixture is stirred with a further 18.0 parts of diatomaceous earth in 79.0 parts of DI water to form a homogeneous paste.

Paste A was mixed with paste B in a weight ratio of 1:4.5. The mixture was tested in accordance with the specification ISO 1563-2. The material had 1'30" of Setting Time and less than 2.89% of permanent deformation.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method of treating a person, the method comprising:
preparing at least one tooth for a dental impression,
inserting an applicator tip of a dental dispenser into a sulcus of the person to a depth of from about 1 mm to about 3 mm,
dispensing a tissue management impression material through the applicator tip into the sulcus using the dental dispenser comprising a cylinder having an outer sleeve, a cartridge, an extrusion tip, a retainer cap, and the applicator tip, wherein the cylinder includes at least one plunger rod therein that interacts with at least one barrel of the cartridge, the cartridge is connected to the extrusion tip, and the retainer cap is secured to the sleeve such that no portion of the cartridge is dislocated from the extrusion tip during the step of dispensing,
placing an impression material onto an impression tray,
applying the impression material in the tray to the at least one tooth after the tissue management material is applied,
curing and bonding the impression material in the tray and the tissue management impression material in the sulcus resulting in a formed, single impression of the at least one tooth, and
removing the formed, single impression from the person.

2. The method according to claim 1, wherein the applicator tip has a canula with a diameter of from about 0.4 mm to about 0.9 mm.

3. The method according to claim 1, wherein the tissue management impression material has a shear strength of from 2000 kPa to 4000 kPa.

4. The method according to claim 1, wherein the applicator tip is inserted into the sulcus without causing trauma to the person.

5. The method according to claim 1, wherein the cartridge of the dental dispenser comprises at least two barrels, where one barrel includes a base and the other barrel includes a catalyst and the extrusion tip includes a mixer therein, such that the tissue management impression material is formed during the step of dispensing.

6. The method of claim 1, wherein the step of dispensing comprises applying a pressure of from 2600 kPa to 5000 kPa to the tissue management impression material.

7. The method of claim 1 comprising dispensing through the applicator tip having a metal canula encased in a plastic material.

8. The method of claim 7, wherein the plastic material is a polypropylene.

9. The method of claim 1 comprising pneumatically dispensing the tissue management impression material from the applicator tip.

10. The method of claim 1 wherein the step of applying an impression material in a tray to the at least one tooth is carried out prior to curing of the tissue management impression material dispensed into the sulcus.

11. The method of claim 1 wherein the step of applying an impression material in a tray to the at least one tooth is carried out subsequent to curing of the tissue management impression material dispensed into the sulcus.

12. The method of claim 1, wherein the applicator tip swivels about an axis transverse to an axis of an attached dispenser.

13. The method of claim 1, wherein the step of preparing comprises applying a pretreatment solution to the at least one tooth.

14. The method of claim 1 further comprising applying a light body viscosity wash to the at least one tooth, the impression material in the tray, or both.

* * * * *